United States Patent [19]

Kuehne

[11] Patent Number: 4,935,509

[45] Date of Patent: Jun. 19, 1990

[54] NOVEL ALKALOIDS

[75] Inventor: Martin Kuehne, Burlington, Vt.

[73] Assignees: University of Vermont; State Agricultural College, Burlington, Vt.

[21] Appl. No.: 363,652

[22] Filed: Jun. 8, 1989

[51] Int. Cl.$^5$ ............................................. C07D 519/04
[52] U.S. Cl. ...................................... 540/478; 548/478
[58] Field of Search ........................ 548/478; 540/478; 514/407, 410

[56] References Cited

U.S. PATENT DOCUMENTS 4,841,045  9/1989  Kuehne ................................ 548/478

Primary Examiner—Anton H. Sutto
Assistant Examiner—D. D. Carr
Attorney, Agent, or Firm—George M. Gould; Bernard S. Leon; William H. Epstein

[57] ABSTRACT

Cycloalkyl and aromatic vinblastine and vincristine derivatives useful as anti-tumor agents.

31 Claims, No Drawings

NOVEL ALKALOIDS

SUMMARY OF THE INVENTION

In accordance with this invention it has been discovered that compounds of the formula

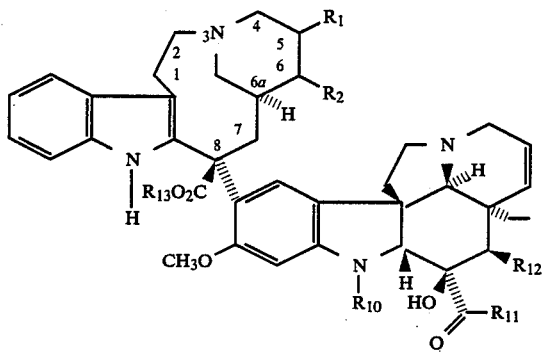

wherein $R_1$ and $R_2$ are in a cis relationship and taken together form $-CH_2-(CH_2)_n-CH_2$; or $R_1$ and $R_2$ taken together with their attached carbon atoms form a benzyl ring; $R_{10}$ is formyl or methyl; n is an integer from 0 to 4; $R_{11}$ is lower alkoxy, $-NR_3R'_3$ or

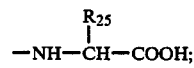

$R_{12}$ is lower alkanoyloxy or hydroxy; $R_{13}$ is lower alkyl; $R_3$ and $R'_3$ are hydrogen or lower alkyl; and $R_{25}$ is that portion of a natural α-amino acid which distinguishes one natural α-amino acid from another; are useful as an anti-tumor agent in the same manner as vinblastine and vincristine.

This invention also produces the corresponding diastereomeric isomers of the compound of formula I which retains the stereo-configuration as shown except that the substituents at the 6a and 8 positions have the opposite stereo-configuration from that shown in formula I. These diastereomeric compounds while not exhibiting any anti-tumor properties are useful in reversing cell resistance to chemotherapeutic agents particularly vincristine and vinblastine.

DETAILED DESCRIPTION

The compounds of the formula I which have the stereo-configuration as shown and their pharmaceutically acceptable salts are useful in inhibiting cancer cell growth and are useful in the same manner as vinblastine and vincristine. A characterization of the new alkaloids of this invention is that certain of these alkaloids do not have the high toxicity of vincristine and vinblastine as will be seen from the results given hereinafter.

For human treatment the compounds of formula I can best be employed intravenously or as infusions. In utilizing the novel compounds of formula I, as anti-tumor agents in mammals, the parenteral route is ordinarily employed. Prior to administration, the drug is customarily mixed with a pharmaceutically suitable carrier. With parenteral administration, the intravenous route is preferred although, with smaller mammals such as mice, the intraperitoneal route may be used. For intravenous administration, isotonic solutions containing 1–10 mg/mL. of a salt of an alkaloid of the formula I are employed. The drug is administered at a dose of from 0.01 to 10 mg/kg and preferably from 0.05 to 1 mg/kg of human body weight once or twice a week or every two weeks depending on both the activity and the toxicity of the drug. An alternative method of arriving at a therapeutic dose is based on body surface area with a dose in the range 0.1 to 10 mg/meter squared of human body surface administered twice weekly or every 7 or 17 days.

As would be expected, the novel compounds encompassed within formula I differ in their anti-tumor spectrum from that of vinblastine and vincristine as the anti-tumor spectra of those compounds differ among themselves, one drug being more effective against certain tumors or classes or tumors and less effective against others. However, in utilizing these compounds clinically, an oncologist may administer them initially by the same route, in the same vehicle and against the same types of tumors as employed clinically with vincristine and vinblastine. Differences in dosage level would, of course, be based on relative oncolytic potency and toxicity.

Tumors against which clinical trial candidates are screened include adenocarcinoma of the breast, bronchogenic carcinoma, adenocarcinoma of the pancreas, ovarian cancer, malignant melanoma, acute myelocytic leukemia, acute lymphocytic leukemia, lymphomatous disease and malignant glioma. A compound of formula I would be tested clinically against one or more of these tumors as well as other tumors known to be susceptible to i.v. administration of vincristine and vinblastine. After its potency, nature and degree of side effects etc. had been established, the drug would be tried against tumors for which there is no therapy. After preliminary tests were concluded and the results published, the drug would be used against tumors susceptible to its action at relatively non-toxic dose levels.

The antitumor properties of the compounds of formula I and their pharmaceutically acceptable salts are seen from comparing vinblastine and vincristine with the following compounds:

| Compound | Name |
|---|---|
| A | (9R,11S)-15-[1,2,4,9,10,11,12,17-octahydro-11-(methoxycarbonyl)-indolo(2',3':6,7)azonino(1,2,-3-bc)isoquinolin-11-yl]vindoline |
| B | (9R,11S)-15-[1,2,4,9,10,11,12,17-octahydro-11-(methoxycarbonyl)-indolo(2',3':6,7)azonino(1,2,-3-bc)isoquinolin-11-yl]N-demethyl-N-formylvindoline |
| C | (4aS,8aR,9R,11S)-15-[1,2,4,4a,5,6,7,8,8a,9,10,-11,12,17-tetradecahydro-11-(methoxycarbonyl)-indolo(2',3':6,7,)azonino(1,2,3-bc)isoquinolin-11-yl]vindoline |
| D | (4aS,8aR,9R,11S)-15-[1,2,4,4a,5,6,7,8,8a,9,10,-11,12,17-tetradecahydro-11-(methoxycarbonyl)-indolo(2',3':6,7,)azonino(1,2,3-bc)isoquinolin-11-yl]N-demethyl-N-formylvindoline |
| E | (4aR,8aS,9R,11S)-15-[1,2,4,4a,5,6,7,8,8a,9,10,-11,12,17-tetradecahydro-11-(methoxycarbonyl)-indolo(2',3':6,7,)azonino(1,2,3-bc)isoquinolin-11-yl] vindoline |
| F | (4aR,8aS,9R,11S)-15-[1,2,4,4a,5,6,7,8,8a,9,10,-11,12,17-tetradecahydro-11-(methoxycarbonyl)-indolo(2',3':6,7,)azonino(1,2,3-bc)isoquinolin-11-yl]N-demethyl-N-formylvindoline |

In the various assays set forth below the colorimetric determination of the number of cells was carried out by the following procedure using MTT.

3-(4,5-dimethylthiazol-2-yl)-2,5-dipenyl tetrazolium bromide (MTT) was prepared as a 5 mg/ml stock solution in phosphate buffered saline, filtered through a 0.22 µm filter and stored for up to two weeks at 4° C. while protected from light. For use in the assay it was diluted to 1 mg/ml in a pH 7.2 solution of phenol-red-free RPMI 1640 tissue culture medium supplemented with 1 mM sodium pyruvate and 50 µg/ml gentamycin. The assay was done in flat bottomed 96-well microtiter plates. Culture medium was removed from the wells by inverting and blotting the plate, fifty µl of MTT solution was added to the cells in each well, and each plate was incubated at 37° C. in an atmosphere of 5% $CO_2$ in air. After incubation, each plate was centrifuged for 5 minutes at 8000×g and excess MTT removed by inverting and blotting. Fifty µl of 95% ethanol was added to each well and the plate was shaken (speed 6.5 for 15 minutes) to solubilize the formazan in each well. The optical density of each well was measured using an automatic plate reader with a test wavelength of 570 nM and a reference wavelength of 630 nM.

The differential in vitro activity of the above compounds as compared to vincristine and vinblastine with regard to P388 wild-type and P388 multiple-drug resistant leukemia was carried out by the following procedure.

Tissue culture-adapted lines of the P388 wild-type and P388 multiple-drug resistant cells (principally resistant to adriamycin) were obtained from the American Type Culture Collection, Rockville, MD. Experiments were conducted in 96-well microtiter plates with 300 cells from either line seeded in a volume of 200 µl of tissue culture medium (RPMI 1640 supplemented to 10% (v/v) with heat-inactivated fetal bovine serum (FBS) and to 200 mM with 1-glutamine). Cells and varying $log^{10}$ dilutions of test compound were added to triplicate sets of wells on the same day and cultures were incubated for 5 days at 37° C. in a humidified atmosphere of 5% $CO_2$ in air. The number of cells per well at the end of the experiment was determined colorimetrically by the reduction of MTT as described above. For purposes of comparison, the concentration of each compound required to reduce the final cell number to one-half of that in drug-free control cultures ($ID_{50}$) is shown.

TABLE I

DIFFERENTIAL ACTIVITY OF TEST COMPOUNDS ON P388 WILD-TYPE AND P388 MULTIPLE-DRUG-RESISTANT CELLS IN VITRO

| Compound | Molar $ID_{50}$ P388/Wild | Molar $ID_{50}$ P3/88/resist. | Fold-resistance[a] |
|---|---|---|---|
| Vincristine | $7.2 \times 10^{-9}$ | $4.1 \times 10^{-7}$ | 57 |
| B | $4.7 \times 10^{-8}$ | $5.1 \times 10^{-7}$ | 11 |
| F | $3.8 \times 10^{-8}$ | $4.5 \times 10^{-7}$ | 12 |
| D | $5.5 \times 10^{-8}$ | $2.0 \times 10^{-6}$ | 36 |
| Vinblastine | $1.9 \times 10^{-8}$ | $3.1 \times 10^{-7}$ | 16 |
| A | $9.5 \times 10^{-8}$ | $4.0 \times 10^{-7}$ | 4 |
| E | $6.8 \times 10^{-8}$ | $4.3 \times 10^{-7}$ | 6 |
| C | $2.2 \times 10^{-7}$ | $8.5 \times 10^{-7}$ | 4 |

[a]Fold-resistance was obtained by dividing the $ID_{50}$ for the resistant cell line by the $ID_{50}$ for the wild-type cell line.

The data in Table I indicates that each of the novel compounds were potent inhibitors of wild-type P388 leukemia cells when compared to the parent vincristine and vinblastine. From the data in Table I the novel compounds of this invention appear to be more useful against multiple drug resistant cells than vinblastine and vincristine.

The in vitro effects of the novel compounds as compared to vinblastine and vincristine on three human colon cancer cell lines and one non-transformed human cell line were determined by the following procedure.

The non-transformed human fibroblast cell line, WI-38 and two of the human colon cancer cell lines, COLO-320-DM and HT-29, were obtained from the American Type Culture Collection, Rockville, MD and the third human colon cancer cell line, OM-1, was supplied by E. I. du Pont de Nemours and Co., Inc., Glenholden, PA. Both OM-1 and COLO-320-DM cells were maintained by serial passage in RPMI 1640 tissue culture medium supplemented to 10% (v/v) with heat-inactivated FBS. HT-29 cells were similarly maintained in McCoys 5A tissue culture medium supplemented with 10% heat-inactivated FBS. COLO-320-DM cells were detached by gentle scraping while HT-29 and OM-1 cells were detached using 0.25% trypsin and 0.05% trypsin, 0.5 mM EDTA solutions respectively. All cultures were incubated at 37° C. in a humidified environment of 5% $CO_2$ in air. Experiments were conducted in 96-well flat-bottomed plates. The initial cell seeds per well for each cell line were 4,000 for WI-38; 2,000 for COLO-320-DM; 750 for HT-29; and 3,000 for OM-1, each in the appropriate tissue culture medium. Cells were plated 24 hours before test compound was added to allow cells to recover from the effects of physical scraping and trypsinization. Varying $log_{10}$ dilutions of drug were added to triplicate sets of wells and cultures were incubated for 6 days at 37° in a humidified atmosphere of 5% $CO_2$ in air. The number of cells per well at the end of the experiment was determined colorimetrically by the reduction of MTT as described above and the results for each compounds shown in Table II. For purposes of comparison, the concentration of each test compound required to reduce the final cell number to one-half of the number in drug-free control cultures ($ID_{50}$) is shown in Table II.

TABLE II

EFFECT OF TEST COMPOUNDS ON THREE HUMAN COLON CANCER CELL LINES AND ONE NON-TRANSFORMED HUMAN FIBROBLAST CELL LINE IN VITRO

| Compound | $ID_{50}$ WI-38 fibroblast | COLO-320 | HT-29 | OM-1 |
|---|---|---|---|---|
| Vincristine | $7 \times 10^{-8}$ | $4 \times 10^{-7}$ | $3 \times 10^{-8}$ | $5 \times 10^{-8}$ |
| B | $1 \times 10^{-7}$ | $3 \times 10^{-7}$ | $2 \times 10^{-8}$ | $6 \times 10^{-8}$ |
| F | $1 \times 10^{-7}$ | $4 \times 10^{-7}$ | $3 \times 10^{-8}$ | $2 \times 10^{-8}$ |
| D | $4 \times 10^{-7}$ | $4 \times 10^{-7}$ | $4 \times 10^{-8}$ | $6 \times 10^{-8}$ |
| Vinblastine | $5 \times 10^{-8}$ | $5 \times 10^{-8}$ | $3 \times 10^{-8}$ | $5 \times 10^{-8}$ |
| A | $4 \times 10^{-7}$ | $4 \times 10^{-7}$ | $3 \times 10^{-8}$ | $4 \times 10^{-7}$ |
| E | $3 \times 10^{-7}$ | $3 \times 10^{-7}$ | $3 \times 10^{-7}$ | $4 \times 10^{-7}$ |
| C | $5 \times 10^{-7}$ | $4 \times 10^{-7}$ | $3 \times 10^{-7}$ | $4 \times 10^{-7}$ |

The above data showed that the novel test compounds of this invention were no more effective against colon cancer than their parent compounds vinblastine and vincristine. Each of the test compounds were shown as potent as vinblastine and vincristine at inhibiting the growth of non-transformed fibroblasts and that of colon cancer cell lines. In this respect, the novel test compounds, of this invention were found not to be superior to vinblastine or vincristine.

The in vivo effect of the novel compounds of this invention against P388 leukemia as compared to vinblastine and vincristine, were compared by the following procedure.

P388 murine leukemia cells were obtained from Southern Research Institute, Birmingham, Ala., and were maintained by serial i.p. passage in C57BL/6 mice. Female (C57BL/6×DBA/2) $F_1$ (BDF) mice of 6-8 weeks of age from Jackson Laboratories, Bar Harbor, Maine, received $1 \times 10^6$ P388 cells by i.p. inoculation on day 0. Compounds were dissolved in saline and administered i.p. to 10 tumor-bearing mice per dose level on days 0-4 and 7-9 using 5 to 10 $\log_2$ dilutions from a concentration known to be toxic. From the resulting data, the dose which was lethal to 50% of mice ($TD_{50}$) and the dose which resulted in 50% long term survivors ($ED_{50}$), as measured by a life span at least 250% longer than non-treated controls, were determined for each test compound. The therapeutic index (T.I.) for each compound was calculated by the formula:

$$\frac{TD_{50} \text{ in mg/kg}}{ED_{50} \text{ in mg/kg}}.$$

The results of this procedure with each of the compounds are given in Table III.

TABLE III

EFFECT OF NOVEL COMPOUNDS ON MICE BEARING P388 LEUKEMIA

| Compound | $TD_{50}$ (mg/kg) | $ED_{50}$ (mg/kg) | T.I. |
|---|---|---|---|
| Vincristine | 1.0 | 0.17 | 5.9 |
| B | 0.092 | 0.02 | 4.6 |
| F | 0.045 | 0.016 | 2.8 |
| D | 0.045 | 0.043[a] | 1.1 |
| Vinblastine | 0.79 | 0.41 | 1.9 |
| A | 0.28 | * | <1 |
| E | 0.18 | * | <1 |
| C | 0.10 | 0.10[a] | 1.0 |

[a]Extrapolated values.
*50% long term survivors were not obtained at any dose, see text.

Efficacy of the compound against leukemia in animals as documented by data summarized in Table III which reveals that Compound B and Compound F cured 50% of tumor-bearing mice at doses which were not toxic. The efficacy of the remaining compounds is clearly documented by the fact that each increased the mean survival time of tumor-bearing mice in a dose-dependent manner. Table IV shows the increase in mean survival time at the optimal dose of each compound employed. The percent increase in mean survival time (MST) which appears in Table IV was calculated by the following formula:

%increase in $MST =$ $$\frac{\text{drug-treated survival time} - \text{control survival time}}{\text{control survival time}} \times 100$$

TABLE IV

NOVEL VINCA ALKALOIDS ENHANCE THE SURVIVAL OF MICE BEARING 388 LEUKEMIA

| Treatment | Dose (mg/kg) | Mean Survival Time (days) | Increase in MST (%) |
|---|---|---|---|
| Vehicle | — | 10.7 | — |
| D | 0.015 | 26.5 | 148 |
| Vehicle | — | 9.6 | — |
| A | 0.12 | 19.7 | 105 |
| Vehicle | — | 10.1 | — |
| E | 0.12 | 21.5 | 113 |
| Vehicle | — | 10.1 | — |
| C | 0.06 | 21.1 | 109 |

Useful non-toxic acids for forming acid addition salts with the compounds of formula I include inorganic acids such as hydrocloric acid, nitric acid, phosphoric acid, sulfuric acid, hydrobromic acid, hydroiodic acid, phosphorous acid and the like, as well as salts of non-toxic organic acids including aliphatic mono and dicarboxylates, phenyl-substituted alkanoates, hydroxy alkanoates and alkandioates, aromatic acids, alphatic and aromatic sulfonic acids, etc. Such pharmaceutically acceptable salts thus include the sulfate, bisulfate, sulfite, bisulfate, nitrate, phosphate, monohydrogenphosphate, dihydrogen-phosphate, metaphosphate, phosphite, pyrophosphate, chloride, bromide, iodide, acetate, propionate, decanoate, caprylate, acrylate, formate, isobutyrate, caproate, heptanoate, propionate, oxalate, malonate, succinate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzene-sulfonate, toluenesulfonate, chlorobenzenesulfonate, xylenesulfonate, phenylacetate, phenylpropionate, phenylbutyrate, citrate, lactate, 2-hydroxybutyrate, glycollate, maleate, tartrate, methanesulfonate, propane-sulfonate, naphthalene-1-sulfonate, naphthalene-2-sulfonate and the like salts.

The corresponding diastereomers of formula I having the stereo-configuration as shown in formula I with the exception that the substituents at the 6a and 8 positions have the opposite stereo-configuration from that shown in formula I are produced by the process of forming the compound of formula I. These diastereomers have not been found to be active in inhibiting or reducing tumor growth as the compounds of formula I. However, it has been found that these diastereomers when applied to tumor cells which have been rendered resistant to chemotherapeutic agents such as vincristine and vinblastine reverse this resistance and cause the cells to be responsive once again to the action of vincristine or vinblastine. In a course of chemotherapy these diastereomers can be administered along with the compounds of formula I above to prevent the formation of resistance by the tumor cells to the agents of formula I.

The term lower alkylidenedioxy designates a lower alkylidenedioxy substituent where lower alkylidene contains from 1 to 7 carbon atoms. Among the preferred lower alkylidenedioxy substituents are included isopropylidenedioxy.

Where a formyl group is protected through the formation of an acetal, the acetal can be formed with any conventional alcohol or glycol to produce an acetal which upon hydrolysis yields the formyl group. Among the conventional alcohols used to produce the acetals are the mono-hydroxy alcohols such as methanol and ethanol as well as other lower alkanols and dihydroxy alcohols, or glycols which produce cyclic acetals such as lower alkylene glycols including ethylene glycol, etc. and dihydroxy lower alkanes containing 2 to 7 carbon atoms such as 1,3-dihydroxypropane, 1,4-dihydroxy butane, etc.

The hydrolyzable ether groups can be any ether protecting groups, which when subjected to cleavage form a hydroxy group. A suitable ether protecting group is, for example, the tetrahydropyranyl ether, or 4-methyl-5,6-dihydro-2H-pyranyl ether. Others are arylmethyl ethers such as benzyl, benzylhydryl, or trityl ethers or alpha-lower alkoxy lower alkyl ether, for example, methoxymethyl, or tri(lower alkyl)silyl ethers such as trimethyl silyl ether or dimethyl-tert-butyl silyl ether. The preferred ethers which are removed by acid catalyzed cleavage are t-butyl and tetrahydropyranyl and the tri(loweralkyl)silyl ethers, particularly dimethyl-tert-butyl silyl ether, which may be removed by reaction with a fluoride such as tetrabutyl ammonium fluoride. Acid catalyzed cleavage is carried out by treatment with a strong organic or inorganic acid. Among the preferred inorganic acids are the mineral acids such as sulfuric acid, hydrohalic acid, etc. Among the preferred organic acids are lower alkanoic acids such as acetic acids, para-toluene sulfonic acid, etc. The acid catalyzed cleavage can be carried out in an aqueous medium or in an organic solvent medium. Where an organic acid is utilized, the organic acid can be the solvent medium. In the case of t-butyl ethers, an organic acid is generally utilized with the acid forming the solvent medium. In the case of tetrahydropyranyl ethers, the cleavage is generally carried out in an aqueous medium. In carrying out this reaction, temperature and pressure are not critical and this reaction can be carried out at room temperature and atmospheric pressure.

The leaving group can be any conventional leaving group. Among the conventional leaving groups which are preferred are tosyloxy, mesyloxy and halogen. With respect to utilizing an amino protecting group, any conventional amino protecting group which can be removed by hydrogenolysis or photochemical cleavage can be utilized in accordance with this invention. Among the preferred amino protecting groups are included trityl, o-nitrobenzyl, benzyl, and diphenylmethyl, etc.

As used throughout this application the term "lower alkyl" designates monovalent saturated straight or branched chain aliphatic hydrocarbon groups containing from 1 to 7 carbon atoms such as ethyl, methyl, n-propyl, isopropyl, n-butyl, isobutyl. The term "lower alkylene" designates a divalent saturated aliphatic straight or branched chain hydrocarbon radical containing 1 to 4 carbon atoms such as methylene or ethylene. The term "halogen" or halide includes all four halogens or halides such as chlorine, bromine, fluorine and iodine with chlorine, bromine and iodine being preferred. The term "lower alkanoyl" designates alkanoyl groups derived from alphatic monocarboxylic acids containing from 1 to 7 carbon atoms such as acetyl, butyryl, pivaloyl, etc. The term "lower alkoxy includes lower alkoxy substituents containing from 1 to 7 carbon atoms such as methoxy, ethoxy, n-propoxy, isopropoxy.

In the pictorial representation of the compounds given throughout this application, a thickened taper line (▬) indicates a substituent which is in the beta-orientation (above the plane of the molecule), a dotted line (≡) indicates a substituent which is in the alpha-orientation (below the plane of the molecule) and a wavy line ($\sim$) indicates a substituent which is in either the alpha- or beta-orientation or mixtures of these isomers.

When $R_1$ and $R_2$ form $-CH_2(-CH_2)_n-CH_2-$, the compound of formula I covers compounds wherein $R_1$ and $R_2$ are both in the beta position or both in the alpha position with respect to the nitrogen containing ring to which they are attached. Hence $R_1$ and $R_2$ are both cis with respect to each other.

In accordance with preferred embodiment of this invention in the compound of formula I, $R_{13}$ is methyl and $R_{12}$ is hydroxy or acetoxy and $R_{11}$ is methoxy. When $R_{11}$ is the residue of a natural alpha-amino acid, $R_{11}$ can be any one of the twenty natural amino acids. Among the preferred α-amino acids which are represented by

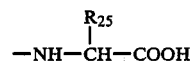

through the removal of a hydrogen from α-amino group of these acids are glycine, alanine, valine, leucine, phenylalanine, trysosine, arginine, proline and tryptophan, with tryptophan being especially preferred.

As used through the specification, "A" designates the vindoline containing residue:

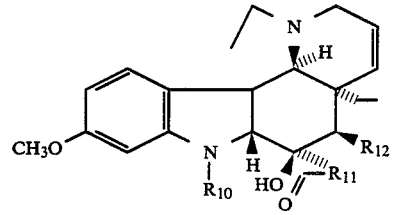

wherein $R_{10}$, $R_{11}$ and $R_{12}$ are as above.

The compound of the formula

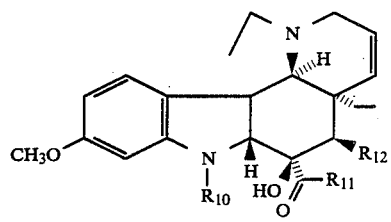

(II)

utilized as a starting material where $R_{11}$ is hydroxy can be converted to the compound of formula II where $R_{11}$ is

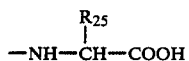

by reaction with a natural α-amino acid. Any of the α-amino acids such as those already mentioned can be utilized in this reaction. This reaction is carried out under conditions conventionally utilized for forming peptide bonds. By reacting the compound of formula II where $R_{11}$ is hydroxy with a suitable amine by conventional amidation of an organic acid $R_{11}$ can be converted from hydroxy to $-NR_3R_4$ where $R_3$ and $R_4$ are as above. Furthermore in the compound of formula II which is utilized as starting material, $R_{10}$ is methyl. This methyl substituent is carried through all of the intermediates until their conversion to the compound of formula I. The compound of formula I where $R_{10}$ is methyl can be converted to the compound of formula I where $R_{10}$ is formyl by conventional oxidation procedures for oxidizing vinblastine type compounds to vincristine type compounds such as those disclosed in U.S. Pat. No. 4,143,041, Mar. 6, 1969—Thompson.

When in the compound of formula I, $R_1$ and $R_2$, taken together form $-CH_2-(CH_2)_n-CH_2$, the compound of formula I has the formula

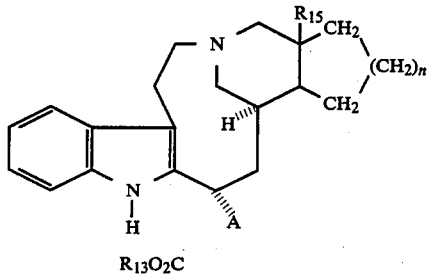

I-A wherein A, n and $R_{13}$ are as above and $R_{15}$ and $R_{16}$ are hydrogen both being in the cis-position.

When in the compound of formula I $R_1$ and $R_2$ taken together with the attached carbon atoms form a phenyl ring the compound of formula I has the following formula:

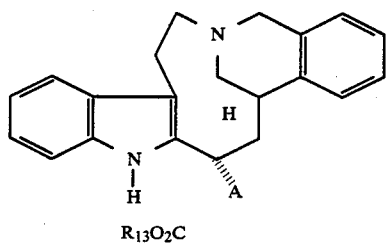

I-B wherein A, n and $R_{13}$ are as above.

The compound of formula I as well as the compound of formula I-A and I-B can be prepared from compounds of the formula:

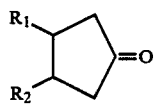

III wherein $R_1$ and $R_2$ are as above.

Via an intermediate of the formula:

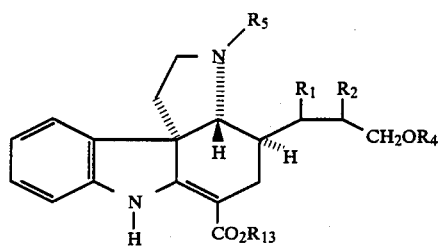

IV wherein $R_1$, $R_2$ and $R_{13}$ are as above $R_5$ is a amino protecting group and $R_4$ is a hydroxy protecting group removable by acid hydrolysis or acid catalyzed cleavage.

The compound of formula III is converted to the compound of formula IV via the following reaction scheme.

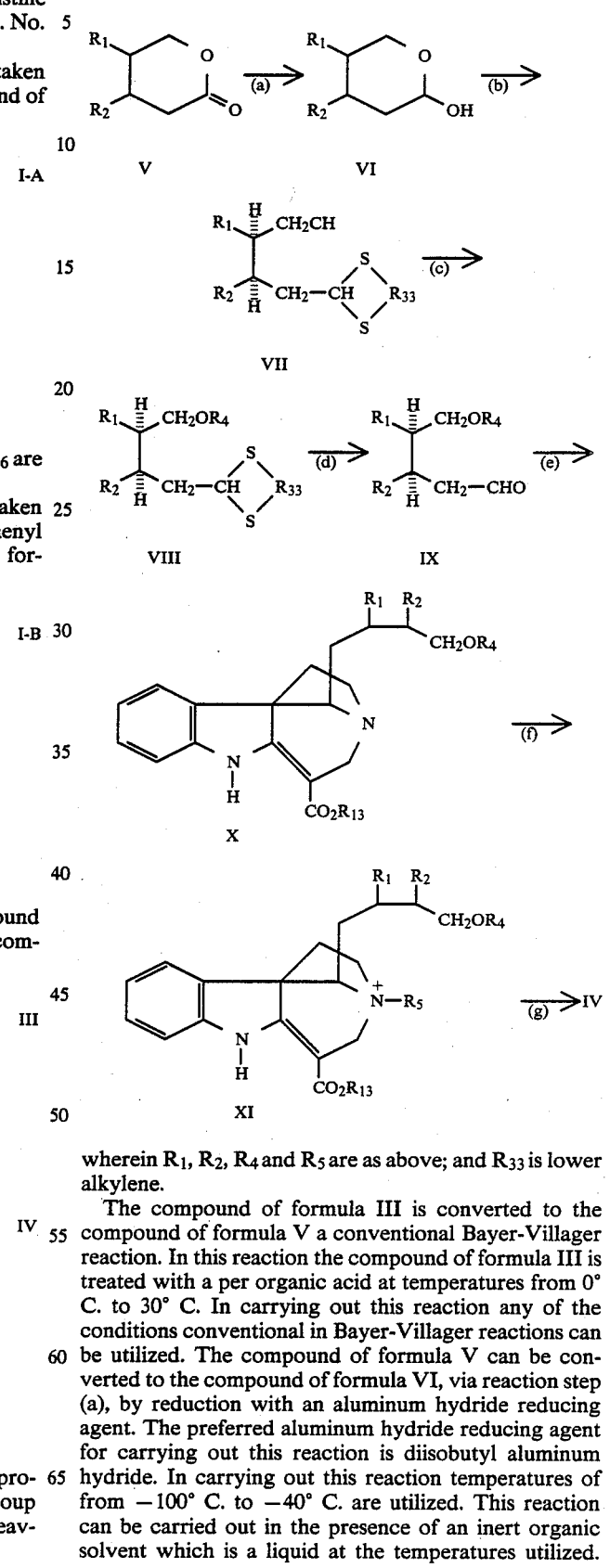

wherein $R_1$, $R_2$, $R_4$ and $R_5$ are as above; and $R_{33}$ is lower alkylene.

The compound of formula III is converted to the compound of formula V a conventional Bayer-Villager reaction. In this reaction the compound of formula III is treated with a per organic acid at temperatures from 0° C. to 30° C. In carrying out this reaction any of the conditions conventional in Bayer-Villager reactions can be utilized. The compound of formula V can be converted to the compound of formula VI, via reaction step (a), by reduction with an aluminum hydride reducing agent. The preferred aluminum hydride reducing agent for carrying out this reaction is diisobutyl aluminum hydride. In carrying out this reaction temperatures of from $-100°$ C. to $-40°$ C. are utilized. This reaction can be carried out in the presence of an inert organic solvent which is a liquid at the temperatures utilized.

Generally it is preferred to utilize solvents such as tetrahydrofuran, chlorinated hydrocarbons such as methylene chloride, and aromatic hydrocarbons such as toluene and benzene. The compound of formula VI is converted to the compound of VII, via reaction step (b), by treating the compound of formula VI with an alkane dithiol. Generally this reaction is carried out at temperatures of from 0° C. to 30° C. with room temperature being especially preferred. This reaction can be carried out in an inert organic solvent with the solvents mentioned in connection with the reaction of step (a) being especially preferred.

The compound of formula VII is converted to the compound VIII via reaction step (c) by converting the free hydroxy group to a protected hydroxy group. $R_4$ can be any conventional hydroxy protecting group. Generally it is preferred to utilize protecting groups which can be removed to produce the resulting hydroxy group by acid hydrolysis or acid or base catalyzed cleavage. Among the preferred hydroxy protecting groups are the lower alkanoyl and triloweralkyl silyl with acetyl and dimethyl-tert-butylsilyl being especially preferred as the substituent $R_4$. Any conventional method of forming these hydroxy protecting groups can utilized to carry out the reaction of the step (c). The compound of formula VIII is converted to the compound of formula IX by conventional acid hydrolysis of thioacetals. Any method of conventional reaction with mercuric salts or acid hydrolysis of thioacetals can be utilized in carrying out the reaction of step (d).

In preparing the compound of formula X, via reaction step (e) either the compound of formula IX or the compound of formula VIII can be reacted with a compound of the formula

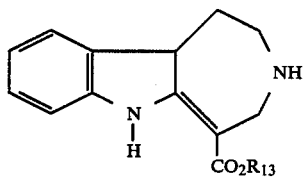

XIII where $R_{13}$ is as above;

In carrying out the reaction of step (e), the compounds of formula VIII or the compound of formula IX are combined with the compound of formula XIII in the presence of an inert organic solvent. Any conventional inert organic solvent can be utilized with lower alkanol solvents being especially preferred. In carrying out this reaction, temperature and pressure are not critical and this reaction can be carried out at room temperature. However, if desired, elevated or reduced temperatures can be utilized.

The compound of formula X can be converted to the compound of formula XI via reaction step (f), by protecting the amino group in the compound of formula X with a suitable nitrogen or amino protecting group such as benzyl. This reaction is carried out in the usual manner by treating the compound of formula X with benzyl bromide. Any conventional nitrogen or amino protecting groups such as those mentioned hereinbefore can be utilized in forming the compound of formula XI. Generally this reaction carried out by utilizing any of the conditions conventionally in forming protected amino groups.

The compound of formula XI is converted to the compound of formula IV, via step (g), by treating the compound of formula XI with a base in an organic solvent. Any conventional base can be utilized to carry out this reaction. The preferred bases are the tri(loweralkyl) amines such as triethyl amine as well as any of the other conventional amine bases. In carrying out this reaction, temperature and pressure are not critical and this reaction can be carried out at room temperature, i.e., 20°-30° C. However, it is generally preferred to carry out this reaction at the reflux temperature of the reaction mixture. In carrying out this reaction any conventional organic solvent can be utilized. Generally it is preferred to utilize the lower alkanol as the solvent such as ethanol, etc.

If in the compound of formula IV, $R^1$ and $R^2$ form $-CH_2-(CH_2)_n-CH_2-$, and n is as above, the compound of formula IV has the following structure:

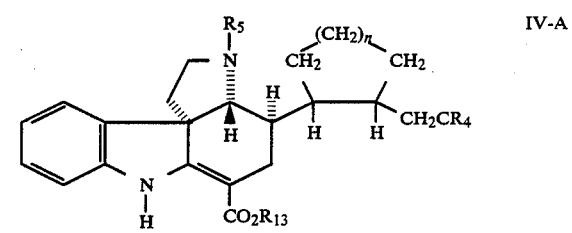

IV-A wherein n, $R_4$, $R_5$ and $R_{13}$ are as above and the hydrogen substituents illustrated at 1 and 2 have a cis configuration.

The compound of formula IV-A has two diastereomers which have the following structure.

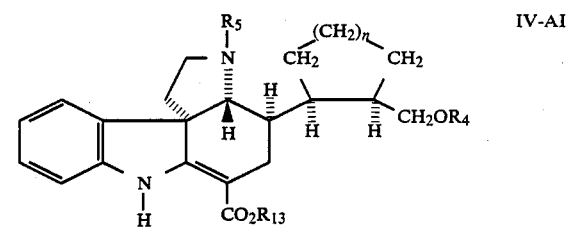

IV-A1 and

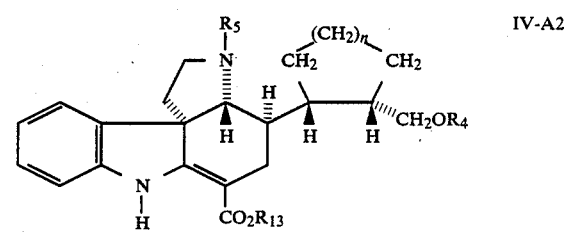

IV-A2 wherein n, $R_4$, $R_5$ and $R_{13}$ are as above.

The compound of IV-A may, if desired, be separated into the compound of IV-A1 and IV-A2 by chromatography. Any conventional method of chromatography can be used to affect this separation.

The compound of formula IV-A either unseparated diasteromers IV-A1 and IV-A2 or as a separated diasteromer IV-A1 or IVA2 can be converted to the compound of formula I-A via the following reaction scheme

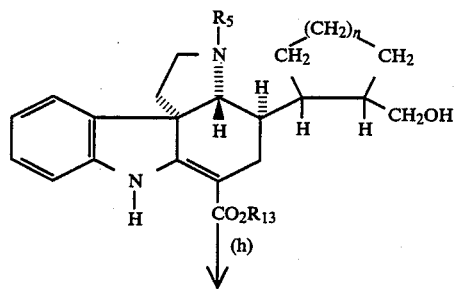

(h)

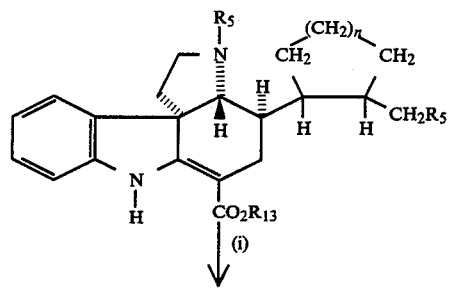

(i)

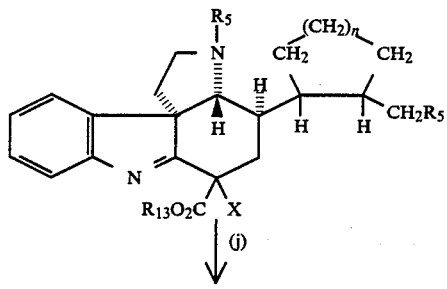

(j)

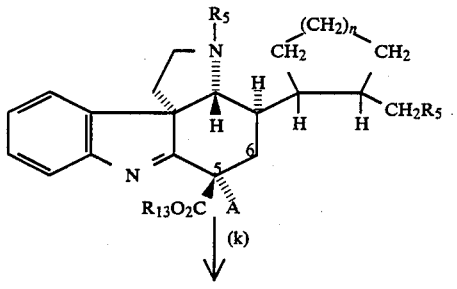

(k)

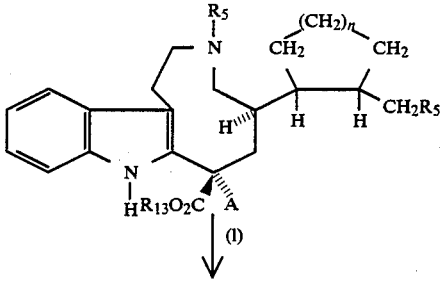

(l)

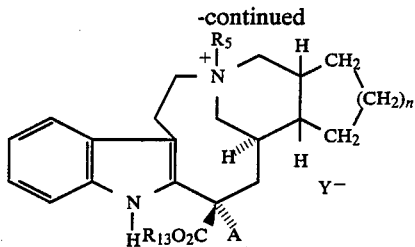

XV

XVI

XVII

XVIII

XIX

XX wherein n, A, $R_5$ and $R_{13}$ are as above; $R_5$ is a leaving group; X is halogen and Y is an anion;

The compound of formula IV-A is converted to the compound of formula XV by acid hydrolysis or acid or base catalyzed cleavage. Any conventional method of acid hydrolysis or acid catalyzed cleavage can be used depending upon the protecting group $R_4$. When $R_4$ is trialkylsilyl, the fluoride ion such as tetraalkylammonium fluoride is used for cleavage.

The compound of formula XV is converted to the compound of formula XVI, via step (h), by converting the terminal hydroxy group in the compound of XV to a leaving group such as mesyloxy, halogen or tosyloxy. Therefore, $R_6$ represents a halogen or a mesyloxy or tosyloxy group. Any conventional method of converting a a primary hydroxy group to a halogen, tosyloxy or mesyloxy group can be utilized to carry out the conversion illustrated in step (h).

The compound of formula XVI is converted to the compound of formula XVII, via reaction step (i), by treating the compound of XVI with a halogenating agent such as an organic or inorganic hypohalite preferably calcium hypohalite, sodium hypohalite or t-butyl hypohalite in the presence of tertiary amine base. Any conventional tertiary amine base can be utilized to carry out this reaction. Among the preferred tertiary amine bases are the tri-lower alkyl amines and the cyclic tertiary amines. Among the preferred cyclic tertiary amines are included N-loweralkylpyrrolidine, N-loweralkyl-piperidine, N,N-di-loweralkylaniline, pyridine, etc. In carrying out this reaction an inert organic solvent can be utilized. On the other hand, the amine base can act as an solvent medium. If it is desired to utilize the solvent, generally aprotic solvents such as halogenated hydrocarbons, ethers and dimethylformamide are preferred. In carrying out this halogenation, temperature and pressure are not critical and this reaction can be carried out at room temperature and atmospheric pressure, with temperatures of $-40°$ C. to 30° C. being generally preferred.

In the next step of the process of this invention the compound of formula XVII is condensed with the compound of formula II to produce the compound of formula XVIII via reaction step (j). In this manner the compound of formula XVIII is produced. In condensing the racemic compound of formula XVII with the compound of formula II, one produces the compound of formula XVIII as a mixture of two diastereomers, with one diastereomers having the configurations as shown and the other having the opposite stereo-configuration at all positions from that shown in the compound of formula XVIII. However in the two diastereomers that are formed there is no difference in the chiral positions of the A moiety designating the vindoline containing residue "A". Through the process of step (j) one produces the compound of formula XVIII as a mixture of the aforementioned diastereoisomers.

This diastereoisomeric. mixture can be separated utilizing conventional means such as chromatography to produce the compound of formula XVIII having the configuration at the chiral positions as shown in the formula XVIII.

For producing the corresponding diastereomer of formula I which retains the stereo-configuration as shown in formula I except that the substituents at the 6a and 8 positions have the opposite configuration, the diastereoisomeric mixture produced in step (j) can be separated at this stage or at any other stage in the preparation of the compound of formula I-A. The compound of formula XVIII as shown produces the compound of formula I-A. The other diastereoisomer of formula XVIII produces the corresponding diastereomer of formula I-A having the same chiral configuration of the compound of formula I-A except that the substituents at 6a and 8 positions have opposite stereo-configurations from that shown in formula I.

The condensation of the compound of formula XVII with the compound of formula II, via reaction step (j), to produce the compound of formula XVIII is carried out in the presence of an aprotic solvent. In carrying out this reaction any conventional aprotic solvent can be utilized. Among the conventional aprotic solvents are aldehydes and ketones such as acetone, methyl ethyl ketone, etc. Other aprotic solvents which are also preferred include ethers such as dioxane and diethyl ether. In accordance with a preferred embodiment of this invention, this reaction takes place in the presence of an acid or with a salt of the compound of II with an acid. Any conventional acid can be used in carrying out this reaction. The preferred acids are $HBF_4$ and hydrohalic acids such as HCl and HBr. In carrying out this reaction it is also generally preferred that condensation take place in the presence of a silver salt. Any conventional silver salt which reacts with halides can be utilized in this reaction. Among the preferred silver salts are silver nitrate, silver tetrafluoroborate, silver perchlorate. In carrying out this reaction, temperature and pressure are not critical and this reaction can be carried out at room temperature and atmospheric pressure. On the other hand, higher or lower temperatures can be utilized. Generally it is preferred to carry out this reaction at a temperature of from $-70°$ C. to $+20°$ C.

The compound of formula XVIII can be converted to a compound of formula XIX, via the reaction step (k). This conversion is carried out by treating the compound of formula XVIII with an alkali metal borohydride in the presence of an acid. Any conventional organic acid can be used in this conversion. Among the organic acids are included formic acid and acetic acid, with acetic acid being preferred. In carrying out this reaction, any conventional organic acid can be utilized as the solvent. Furthermore, in carrying out this reaction, temperature and pressure are not critical and this reaction can be carried out at room temperature and atmospheric pressure. On the other hand, if desired elevated or lower temperatures can be utilized.

In producing the compound of formula XX, by reaction step (1), the compound of formula XIX is heated in a organic solvent at a temperature of from $35°$ C. to $100°$ C. In carrying out this reaction, any conventional inert organic solvent can be utilized with aromatic hydrocarbons such as toluene and benzene or ether solvents or lower alkanols such as methanol being preferred. Among the solvents which can be utilized are solvents boiling above $35°$ C. However, lower boiling solvents can also be utilized if the reaction is carried out in a sealed vessel. The leaving group $R_6$ in this reaction becomes the anion Y' in the compound of formula XX upon formation of the quaternary salt. The compound of formula XX is converted to the compound of formula I-A by removal of the amino protection group by hydrogenolysis or photochemical cleavage. Any of conventional methods utilized in removing amino protecting group by these procedures can be utilized in carrying out this reaction.

Alternatively the compound of formula I-A can be obtained from the compound of formula XIX by removing the amino protecting group $R_5$ to produce the compound of formula XIX where $R_5$ is hydrogen. Any conventional method of removing an amino protecting group such as by hydrogenolysis or photochemical clevage can be utilized to produce the compound of formula XIX where $R_5$ is hydrogen. The resulting compound of formula XIX where $R_5$ is hydrogen can be cyclized to the compound of formula IA simply by allowing it to stand at room temperature for an extended period. Cyclization can best be achieved by heating in the presence of a solvent. Any conventional organic solvent can be used, with toluene and methanol being preferred. Generally it is preferred to carry out the cyclization in a solvent at the reflux temperature of the solvent.

When in the compound of formula IV, $R_1$ and $R_2$ taken together with their attached carbon atoms to form an aromatic ring, the compound of formula IV has the following formula

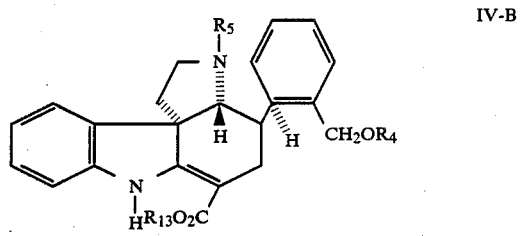

IV-B wherein $R_{13}$, $R_4$ and $R_5$ are as above.

The compound of formula IV-B is converted to the compound of formula I-B via the following reaction scheme.

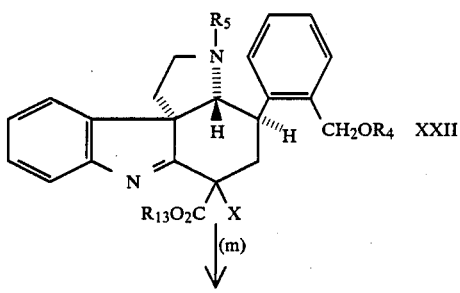

XXII

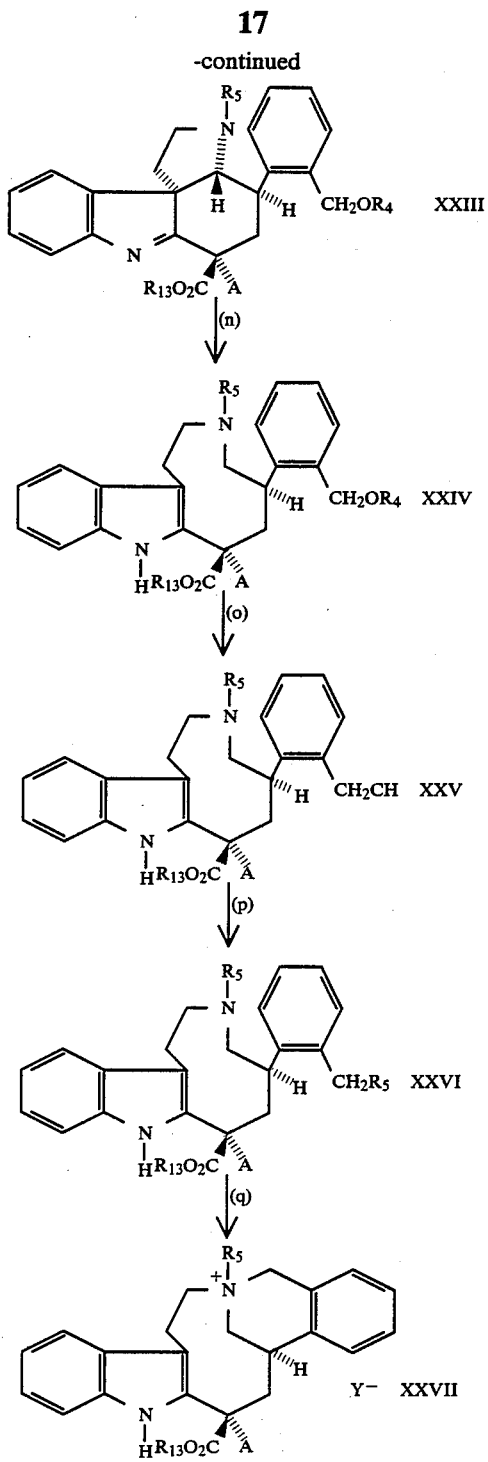

wherein A, X, $R_4$, $R_5$, $R_6$, $R_{13}$, and Y is as above.

The compound of formula IV-B is converted to the compound of formula XXII by halogenation with a hypohalite such as t-butyl hypochlorite, sodium hypochlorite or calcium hypochlorite in the presence of a tertiary amine. This reaction is carried out in the same manner as described hereinbefore in connection with reaction step (i). The conditions described in connection with reaction step (i) can be utilized in converting the compound of formula IV-B to the compound of formula XXII.

The compound of formula XXII is condensed with the compound of formula II, via reaction step (m), to produce the compound of formula XXIII. This reaction is carried out in the same manner as described in connection with reaction of step (j). Any of the conditions described in connection with reaction step (j) can be utilized in condensing compounds of formula XII with a compound of formula II to produce the compound of formula XXIII. In accordance with this invention, the compound of formula XXIII with the configuration as shown can be produced as a mixture thereof with the corresponding diastereoisomer having the opposite stereo-configuration from that shown. The two diastereoisomers produced by this process have opposite stereo-configuration at all of the chiral centers shown in the compound of formula XXIII. However, in both diatereoisomers produced as a mixture by this process, the moiety A is the same and has the same stereo-configuration as shown. This diastereoisomeric mixture can be separated at this or a later stage in the reaction scheme to produce the compound of formula I-B utilizing conventional means such as chromatography. The diastereoisomeric compounds which have the opposite configuration to that shown in compounds XXIII to XXVII produce the corresponding diastereoisomer of formula I-B having the same stereo-configuration as that of formula I except that the 6a and 8 positions have the opposite configuration from that shown.

The compound of formula XXIII is converted to the compound of formula XXIV, via reaction step (n), by treating the compound of formula XXIII with a alkali metal borohydride in accordance with the conditions hereinbefore described in connection with reaction step (k).

The compound of formula XXIV is converted to the compound of XXV by first removing the hydroxy protecting group by conventional hydrolysis. Any conventional method of hydrolyzing ethers or esters through acid catalyzed cleavage or acid hydrolysis can be utilized to convert the compound of XXIV to the compound formula XXV, via reaction step (o).

The compound of formula XXV is converted, via reaction step (p), to the compound of formula XXVI by any conventional method of converting a hydroxy group to a leaving group such as mesyloxy, tosyloxy or halogens such as chlorine, bromine or iodine. Any of the methods conventional for converting a hydroxy group to any of these conventional leaving groups can be utilized to produce this conversion. The preferred leaving group is tosyloxy.

The compound of formula XXVI is converted to the compound of formula XXVII by heating to a temperature of from 20° C. to 80° C. In accordance with the process of this invention the conversion of the hydroxy group in the compound of formula XXV to a leaving group will produce the compound of formula XXVII directly if temperatures of from 20° C. to 80° C. are utilized. If these temperatures are utilized the compound of formula XXVI is formed as a transitory intermediate. On the other hand, the compound of formula XXVI can be isolated directly if the leaving group is formed at a temperature of from 0° C. to about 5° C. Therefore, depending upon the temperature utilized and the specific leaving group, the compound of formula XXV can be either directly converted to the compound of formula XXVII or can be converted to the compound of formula XXVI which upon heating will produce the compound of formula XXVII.

The compound of formula XXVII can be converted to the compound of formula IB by removing the amino protecting group through subjecting the compound of formula XXVII to hydrogenolysis or photochemical cleavage. In carrying out this reaction any conventional method of hydrogenolysis or photochemical cleavage can be utilized to remove the amino protecting group designated by $R_5$. Alternatively, the removal of the amino protecting group in the compound of formula XXVI produces the compound of formula XXVI where $R_5$ is hydrogen. The compound of formula XXVI where $R_5$ is hydrogen can be cyclized directly to the compound of formula I-B in the manner described in connection with the conversion of the compound of formula XIX to the compound of formula I-A.

The following examples are illustrative but not limitative of the claimed invention. In the example, the ether is diethyl ether and Celite is diatomaceous earth HPLC in the examples designates high pressure liquid chromatography.

EXAMPLE 1

1,4-Dihydro-3H-2-benzopyran-3-one.

To 6.60 g (0.050 mol) of 2-indanone in 50 mL of dry dichloromethane was added 38.0 g (0.45 mol) of powdered anhydrous sodium bicarbonate, followed by 17.0 g (0.10 mol) of m-chloroperoxybenzoic acid. After stirring at 20° C. for 20 hours, further 3.0 g (0.017 mol) of the peracid was added and stirring continued for 24 hours. After addition of 200 mL of 10% aqueous $Na_2S_2O_3$ stirring was continued until two clear phases had formed. The organic solution was separated and the aqueous phase was extracted with two 100 mL portions of dichloromethane. The combined organic solutions were dried ($MgSO_4$) and concentrated under vacuum at 30° C. Solution in a mixture of ether and pentane, filtration and concentration under vacuum gave 6.7 g (90%) of 1,4-dihydro-3H-2-benzopyran-3-one, which could be recrystallized from ether or sublimed at 30°-40° C. (0.24 mm); mp 78°-79° C.; TLC Rf 0.36 ($SiO_2$, $CH_2Cl_2$, brown-orange with iodine).

EXAMPLE 2

3,4-Dihydro-1H-2-benzopyran-3-ol.

To a solution of 3.00 g (0.020 mol) of 1,4-dihydro-3H-2-benzopyran-3-one in 100 mL of dry dichloromethane, cooled to −78° C., was added dropwise, over 1 hour, 24 mL (0.022 mol) of a 1M solution of disobutyl aluminum hydride in dichloromethane. After stirring at −78° C. for 2 hours and at 0° C. for 15 minutes, 100 mL of ether was added, followed by dropwise addition of 1.2N HCl until a pH of 1-2 was reached. Separation of the organic phase, extraction of the aqueous phase with ether and concentration of the combined dried ($MgSO_4$) extracts provided 2.8 g (91%) of 3,4-dihydro-1H-2-benzopyran-3-ol. This product decomposes on standing or on chromatography on silica gel and consequently was used directly for the next reaction step. TLC $R_f$ 0.13 ($SiO_2$, $CH_2Cl_2$, brown-orange CAS and heat).

EXAMPLE 3

Racemic Methyl (3aRS,4RS,11bSR)-3-(Benzyl)-1,2,3,3a,4,5-hexahydro-4-[2-hydroxymethyl)phenyl]-3-(phenylmethyl)-7H-pyrrolo[2,3-d]carbazole-6-carboxylate.

To 3.66 g (0.015 mol) of methyl 1,2,3,4,5,6-hexahydroazepino (4,5-b)-indole-5-carboxylate in 200 mL of dichloromethane was added, in one portion, 1.95 g (0.014 mol) of the lactol 3,4-dihydro-1H-2-benzopyran-3-ol followed by 90 mg (0.0015 mol) of boric acid. The mixture was stirred at room temperature for 3 days, when TLC showed complete reaction of the lactol. The mixture was concentrated under vacuum and the residual solid foam was dissolved in 150 mL of dry chloroform. After addition of 6 mL of benzyl bromide the reaction mixture was heated at reflux for 8 hours, resulting in formation of a heterogeneous suspension. Concentration under vacuum and trituration of the residue with a 1:1 parts by volume ether: pentane mixture, followed by addition of more pentane, deposited a solid. After washing the solid with pentane, it was added to 150 mL of dry methanol and 8 mL of triethylamine. The mixture was heated at reflux for 10 hours and the solution was then concentrated under vacuum. Partioning the residue between dichloromethane and 10% aqueous sodium carbonate, followed by adsorption of the dried ($MgSO_4$) organic extract on 40 g of silica gel, which was then applied to a 300 g silica gel dry column, and elution with 1:4 parts by volume ethyl acetate: pentane, gave 3.5 g (50% yield) of racemic methyl (3aRS,4RS,11bSR)-3-(benzyl)-1,2,3,3a,4,5-hexahydro-4-[2-(hydroxymethyl)phenyl]-3-(phenylmethyl)-7H-pyrrolo[2,3-d]carbazole-6-carboxylate, which crystallized from ether with mp 181°-182° C. TLC $R_f$ 0.25 ($SiO_2$, ethyl acetate: pentane 1:2, CAS blue, yellow center).

EXAMPLE 4

Racemic Methyl (3aRS,4RS,11bSR)-3-(Benzyl)-4-[2-(t.butyldimethylsilyloxymethyl)phenyl]-1,2,3,3a,4,5-hexahydro-7H-pyrrolo[2,3-d]carbazole-6-carboxylate.

To a solution of 1.492 g (3.20 mmol) of racemic methyl (3aRS,4RS,11bSR)-3-(benzyl)-1,2,3,3a,4,5-hexahydro-4-[2-(hydroxymethyl)phenyl]-3(phenylmethyl)-7H-pyrrolo[2,3-d]carbazole-6-carboxylate in 60 mL of dry dichloromethane was added 0.535 mL (3.84 mmol) of dry triethylamine, followed by dropwise addition of 0.743 mL (3.23 mmol) of t. butyl dimethylsilyl trifluormethanesulfonate. TLC indicated directly completion of the reaction. Water (20 mL) was added, the organic phase separated, and the aqueous portion extracted once with dichloromethane. Concentration of the combined dried ($MgSO_4$) organic solutions and chromatography on 50 g of silica gel, eluting with 1:99 methanol:dichloromethane gave 1.75 g (93%) of racemic methyl (2aRS,4RS,11bSR)-3-(benzyl)-4-[2-(t.butyldimethylsilyloxymethyl)phenyl]-1,2,3,3a,4,5-hexahydro-7H-pyrrolo[2,3-d]carbazole-6-carboxylate.

EXAMPLE 5

Methyl (5R,7S)-3-(Benzyl)-5-[2-(t.butyldimethylsilyloxymethyl)phenyl]-1,2,3,4,5,6,7,8-octahydroazonino[5,4-b]indole-7-(15-vindolinyl)-7-carboxylate and its corresponding (5R,7R)-Diastereomer (1:1).

To a solution of 1.06 g (1.83 mmol) of racemic [methyl(3aRS,4RS,11bSR)]-3-(benzyl)-4-[2-(t.butyldimethylsilyloxymethyl)phenyl]-1,2,3,3a,4,5-hexahydro-7H-pyrrolo[2,3-d]carbazole-6-carboxylate in 30 mL of dry dichloromethane, cooled to 0° C., was added 0.301 mL (2.74 mmol) of triethylamine, followed by 0.320 mL (2.74 mmol) of t.butyl hypochlorite. After stirring for 5 min TLC indicated complete reaction of the starting material. The solution was washed with 10 mL of water and the aqueous wash extracted with 2×20 mL of dichloromethane. The combined organic extracts were dried (MgSO₄), concentrated under vacuum and dissolved in 60 mL of dry acetone. At 0° C., in the dark, 765 mg (1.55 mmol) of vindoline hydrochloride was added in one portion, followed after 5 min at 0° C. by 1.069 g (5.48 mmol) of silver tetrafluoroborate. The mixture was stirred at 0° C. for 30 min and then partitioned between 50 mL of dichloromethane and 100 mL of 3% ammonium hydroxide in brine. Five extractions of the aqueous phase with 50 mL of dichloromethane and concentration of the combined, dried (MgSO₄) extracts under vacuum gave methyl (3aR,4R,11bS,6S)-3-(benzyl)-4-[2-(t.butyldimethylsilyloxymethyl)-phenyl]-2,3,3a,4,5,6-hexahydro-1H-pyrrolo[2,3-d]carbazole-6-(15-vindolinyl)-6-carboxylate and its (3aS,4S,11bR,6R)-diastereomer, in a 1:1 ratio, as a solid foam. This product was dissolved in 50 mL of acetic acid and 987 mg (18.3 mmol) of KBH₄ was added in small portions over 30 min. After further 5 min, the solution was poured into 300 mL of conc. ammonium hydroxide and ice and extracted with 5×50 mL of dichloromethane. Concentration of the dried (MgSO₄) extracts under vacuum and chromatography of the residue on 100 g of silica gel, eluting first with 1:1 parts ethyl acetate:pentane, followed by 2:1 ethyl acetate:pentane, provided 649 mg (41%) of the methyl (5R,7S)-3-(benzyl)-5-[2-(t.butyldimethylsilyloxymethyl)-phenyl]-1,2,3,4,5,6,7,8-octahydroazonino[5,4-b]indole-7-(15-vindolinyl)-7-carboxylate, TLC $R_f$ 0.28 (SiO₂, 1:1 ethyl acetate:pentane, CAS brown-green), followed by 757 mg (47%) of its (5R,7R)-diastereomer, TLC $R_f$ 0.15 (SiO₂, 2:1 ethyl acetate:pentane, CAS brown-green).

EXAMPLE 6

Methyl (5R,7S)-3-(Benzyl)-5-[2-(hydroxymethyl)phenyl]-1,2,3,4,5,6,7,8-octahydroazonino[5,4-b]indole-7-(15-vindolinyl)-7-carboxylate.

To a solution of 564 mg (0.0544 mmol) of the silyl ether, methyl (5S,7S)-3-(benzyl)-5-[2-(t.butyldimethylsilyloxymethyl)phenyl]-1,2,3,4,5,6,7,8-octahydroazonino[5,4-b]indole-7-(15-vindolinyl)-7-carboxylate in 13 mL of tetrahydrofuran was added 6.5 mL of water, followed by 1.87 g (10.9 mmol) of p. toluenesulfonic acid monohydrate. After stirring at 20° C. for 45 min TLC indicated completion of the silyl ether cleavage. Addition of 20 mL of dichloromethane and enough 10% aqueous Na₂CO₃ to adjust the pH to 8-9, separation of phases and extraction with 4×30 mL of dichloromethane, drying (MgSO₄) of the combined extracts and concentration under vacuum provided a crude product, which was chromatographed on 20 g of silica gel, eluting 441 mg (88%) of methyl (5R,7S)-3-(benzyl)-5-[2-(hydroxymethyl)phenyl]-1,2,3,4,5,6,7,8-octahydroazonino[5,4-b]indole-7-(15-vindolinyl)-7-carboxylate with ethyl acetate. TLC $R_f$ 0.21 (SiO₂, ethyl acetate, CAS brown-purple to yellow to blue).

EXAMPLE 7

(9R,11S)-15-[1,2,4,9,10,11,12,17-Octahydro-11-(Methoxycarbonyl)-indolo(2′,3′:6,7)azonino(1,2,3-bc)isoquinolin-11-yl]vindoline To a solution of 350 mg (0.380 mmol) of the alcohol, methyl (5R,7S)-3-(benzyl)-5-[2-(hydroxymethyl)-phenyl]-1,2,3,4,5,6,7,8-octahydroazonino[5,4-b]indole-7-(15-vindolinyl)-7-carboxylate in a 20 mL of dry dichloromethane, at 20° C., was added 0.07 mL (0.493 mmol) of dry triethylamine, followed by 151 mg (0.455 mmol) of p. toluenesulfonic anhydride, in small portions over 30 min. After an additional 5 min, TLC showed complete reaction of the starting alcohol to produce (5R,7S)-3-(benzyl)-5-[2-(tosyloxymethyl)phenyl]-1,2,3,4,5,6,7,8,-octahydroazonino(5,4-h)indole-7-(15-vinolinyl)-7-carboxylate and (9R,11S)-15-[3-benzyl-1,2,4,9,11,12,17-octahydro-11-(methoxycarbonyl)-indolo(2′,3′:6,7)azonino(1,2,3-bc)isoquinolinium-11-yl]vindoline tosylate. From this product, the solvent was evaporated under vacuum and the concentrate dissolved in 30 mL of dry methanol. Under argon, 170 mg of 10% Pd/C was added and the mixture was then stirred under hydrogen for 30 min at 20° C. Filtration through Celite 545 and washing of the catalyst with 1:1 methanole:dichloromethane, concentration under vacuum, partitioning between dichloromethane and 5% aqueous sodium bicarbonate and concentration of the dried (MgSO₄) extract gave a crude product, which was chromatographed on 15 g of silica gel. Elution with ethyl acetate followed by 4:1 parts ethyl acetate:ethanol gave 160 mg (52%) of (9R,11S)-15-[1,2,4,9,10,11,12,17-octahydro-11-(methoxycarbonyl)-indolo(2′,3′:6,7)azonino(1,2,3-bc)isoquinolin-11-yl]vindoline from the second eluent. TLC $R_f$ 0.5 (SiO₁, 4:1 ethyl acetate:ethanol).

EXAMPLE 8

(9R,11S)-15-[1,2,4,9,10,11,12,17-Octahydro-11-(methoxycarbonyl)-indolo(2′,3′:6,7)azonino(1,2,3-bc)isoquinolin-11-yl]N-demethyl-N-formylvindoline To a solution of 10 mg (0.012 mmol) of (9R,11S)-15-[1,2,4,9,10,11,12,17-octahydro-11-(methoxycarbonyl)-indolo(2′,3′:6,7)azonino(1,2,3-bc)isoquinolin-11-yl]vindoline in 6 mL of dry tetrahydrofuran at −65° C. was added dropwise, over 2 min, with rapid stirring a solution of 122 mg of sodium dichromate dihydrate in 0.08 mL of water and 0.083 mL of conc. sulfuric acid, holding the temperature below −55° C. After stirring at −60° to −65° C. for 3 h the mixture was poured into 1.8 mL of 28% ammonium hydroxide dissolved in 10 mL of water, rinsing the reaction flask with 3×5 mL of dichloromethane. After phase separation and extraction of the aqueous portion with 4×5 mL of dichloromethane, the combined organic extracts were washed with 10 mL of 5% aqueous sodium thiosulfate, dried (MgSO₄) and concentrated under vacuum to 9 mg (90%) of the (9R,11S)-15-[1,2,4,9,10,11,12,17-octahydro-11-(methoxycarbonyl)-indolo(2′,3′:6,7) azonino(1,2,3-bc)isoquinolin-11-yl]N-demethyl-N-formylvindoline.

EXAMPLE 9

(2 alpha and 2 beta 3a alpha, 7a alpha)-Octahydro-1H-inden-2-ol.

To a solution of 13.4 g (10.0 mmol) of 2-indanol in 100 mL of dry methanol was added 3.0 g of 5% Rh on carbon under a stream of argon. The solution was shaken in a Parr hydrogenation apparatus under hydrogen at 60 psi and 20° C. for 8 h. The mixture was filtered through Celite 545, rinsing with methanol, and the filtrate concentrated and distilled to give 4.2 g (30%) of (2 alpha and 2 beta 3a alpha, 7a alpha)-octahydro-1H-inden-2-ol, bp 130°-131° C. (18 mm); TLC Rf 0.68, 0.60 (SiO₂, ethyl ether, molybdophosphoric acid-dark blue).

EXAMPLE 10

(3a alpha, 7a alpha)-Octahydro-2H-inden-2-one.

To 33.6 g (155 mmol) of finely ground pyridinium chlorochromate, stirred in 300 mL of dry dichloromethane, was added 7.0 g (50 mmol) of (2 alpha and 2 beta)-octahydro-1H-inden-2-ol in 30 mL of dichloromethane. After stirring for 2 h at 20° C., 300 mL of ether was added, the organic solution decanted from the gummy precipitate and the latter extracted with 5×100 mL of ether. The combined organic solutions were filtered through 450 g of silica gel and the latter washed with ether. Concentration of the filtrates and distillation gave 5.5 g (80%) of (3a alpha, 7a alpha)octahydro-2H-inden-2-one bp 110°–112° C. (18 mm); TLC Rf of 0.29 (SiO$_2$, dichloromethane, molybdophosphoric acid-colorless on blue-green).

EXAMPLE 11

Racemic (4a alpha, 8a alpha)-Octahydro-3H-2-benzopyran-3-one.

To a stirred mixture of 3.16 g (23 mmol) of (3a alpha, 7a alpha)-octahydro-2H-inden-2-one, 17.3 g (207 mmol) of NaHCO$_3$ and 300 mL of dichloromethane was added 9.29 g of 85% m. chloroperoxybenzoic acid in small portions over 15 min. The reaction mixture was stirred for 17 h at 20° C., then 200 mL of 10% aqueous Na$_2$S$_2$O$_3$ was added and, after 15 min, the organic phase was separated. Extraction of the aqueous portion with 2×100 mL of dichloromethane, washing of the combined organic solutions with 10% Na$_2$CO$_3$ and concentration of the dried (MgSO$_4$) solutions under vacuum gave 3.51 g (95%) of racemic (4a alpha, 8a alpha)-octahydro-3H-2-benzopyran-3-one. TLC R$_f$0.40 (SiO$_2$, ethyl ether, iodine-brown).

EXAMPLE 12

Racemic (4a alpha, 8a alpha)-Octahydro-1H-2-benzopyran-3-ol.

To a solution of 2.0 g (13 mmol) of (4a alpha, 8a alpha)(rac)-octahydro-3H-2-benzopyran-3-one in 65 mL of dry dichloromethane was added dropwise, over 30 min, 14 mL (14.3 mmol) of a 1.0M solution of diisobutylaluminum hydride in dichloromethane. After further stirring at −78° C. for 45 min the mixture was warmed to 0° C. over 2 hours, stirred at 0° C. for 10 min, and then 1.0M aqueous HCl was added dropwise until a pH 0-1 was reached. After addition of 60 mL of ether, phase separation and extraction of the aqueous portion with 3×50 mL of ether, the combined organic solutions were washed with 5% KHCO$_3$, dried (MgSO$_4$) and concentrated under vacuum to 1.60 g (80%) of racemic (4a alpha, 8a alpha)-octahydro-1H-2-benzopyran-3-ol. TLC R$_f$ 0.41 (SiO$_2$, ether, molybdophosphoric acid-blue).

EXAMPLE 13

Racemic cis-2-(1,3-Dithiolan-2-yl methyl)cyclohexanemethanol.

To a stirred solution of 1.6 g (10 mmol) of the lactol, (4a alpha, 8a alpha)(rac)-octahydro-1H-2-benzopyran-3-ol in 4.2 mL (49 mmol) of 1,2-ethane dithiol at 0° C. was added dropwise 1.03 mL (12 mmol) of 12N HCl. After 10 min at 0° C. and 2 h at 20° C., further 3.16 mL (36 mmol) of 12N HCl was added and stirring continued for 40 min. The mixture was then partitioned between ice water and 3×50 mL of dichloromethane. The organic extracts were washed with 5% NaHCO$_3$ and brine, dried (MgSO$_4$) and concentrated under vacuum. Column chromatography on 100 g of silica gel, gave 1.50 g of material eluted with dichloromethane and 0.74 g (29%) of the title dithiolan, eluted with ether. The dichloromethane eluate (1.5 g) was heated with 40 mL of benzene and a crystal of p. toluenesulfonic acid at reflux for 3 h. Rechromatography on silica gel and elution with ether gave additional 850 mg (35%) of racemic cis-2-(1,3-dithiolan-2-yl methyl)cyclohexanemethanol (62% total). TLC (SiO$_2$) R$_f$0.11 (dichloromethane), 0.47 (diethyl ether), detection:molybdophosphoric acid-blue.

EXAMPLE 14

Racemic cis-2-(1,3-Dithiolan-2-yl methyl)cyclohexanemethanol acetate.

At 0° C., 290 μL (3.5 mmol) of pyridine was added to 0.740 g (3.18 mmol) of rac-cis-2-(1,3-dithiolan-2-yl methyl)cyclohexanemethanol in 5 mL of dichloromethane, followed by dropwise addition of 235 μL (3.5 mmol) of acetyl chloride. After 15 min at 0° C. and 30 min at 20° C., the reaction mixture was partitioned between water and dichloromethane and the organic solution washed with 1.0N HCl and with 5% KHCO$_3$ solutions, dried (MgSO$_4$) and concentrated under vacuum to 865 mg (98%) of racemic cis-2-(1,3-dithiolan-2-yl methyl)cyclohexanemethanol acetate. TLC R$_f$0.48 (SiO$_2$, dichloromethane, I$_2$-brown).

EXAMPLE 15

Racemic cis-[(2-Acetoxymethyl)cyclohexyl]ethanal.

To a stirred suspension of 432 mg (2.0 mmol) of mercuric oxide in 4.25 mL of tetrahydrofuran and 0.75 mL of water, at 20° C., was added 1.14 mL of 35% HBF$_4$, followed by 290 mg (1.05 mmol) of the dithiolan rac-cis-2-(1,3-dithiolan-2-yl methyl)cyclohexanemethanol acetate. After 5 min 20 mL of dichloromethane was added and the mixture was filtered through Celite 545 with 5×10 mL washes of dichloromethane. The organic solution was then shaken with 10% sodium iodide and 5% potassium bicarbonate solutions, dried (MgSO$_4$) and concentrated under vacuum to 200 mg (95%) of racemic cis-[(2-acetoxymethyl)cyclohexyl]ethanal. TLC R$_f$ 0.37 (SiO$_2$, dichloromethane, 10% H$_2$SO$_4$ in ethanol, pink).

EXAMPLE 16

Racemic methyl 11α and β-cis-[[2-(Acetoxymethyl)cyclohexyl]methyl]-1,2,4,6-tetrahydro-3,10b-methanoazepino[4,5-b]indole-5-carboxylate.

At 20° C., 382 mg (1.93 mmol) of rac-cis-[2-acetoxymethyl)cyclohexyl]ethanol was added to a solution of 313 mg (1.30 mmol) of methyl 1,2,3,4,5,6-hexahydroazepino (4,5-b) indole-5-carboxylate in 10 mL of dichloromethane. After 16 hours the mixture was concentrated under vacuum to provide 516 mg (95%) of the racemic methyl 11α and β-cis-[[2-(acetoxymethyl)cyclohexyl]methyl]-1,2,4,6-tetrahydro-3,10b-methanoazepino[4,5-b]indole-5-carboxylate. TLC R$_f$ 0.72, 0.56 (SiO$_2$, 9:1 dichloromethane:methanol, CAS blue).

EXAMPLE 17

Racemic Methyl [3aRS, 4RS, 11bSR]-4-[1RS,2RS]-[2-(Acetoxymethyl)cyclohexyl]-3-(benzyl)-1,2,3,3a,4,5-hexahydro-7H-pyrrolo[2,3-d]carbazole-6-carboxylate and Racemic Methyl [3aRS, 4RS, 11bSR]-4-[1SR,2SR]-[2-(Acetoxymethyl)cyclohexyl]-3-(benzyl)-1,2,3,3a,4,5-hexahydro-7H-pyrrolo[2,3-d]carbazole-6-carboxylate.

To a solution containing (544 mg, 1.28 mmol) racemic methyl 11α and β-cis-[[2-(acetoxymethyl)cyclohexyl] methyl]-1,2,4,6-tetrahydro-3-,10b-methanoazepino[4,5-b]indole-5-carboxylates in mL of dichloromethane was added 350 μL (2.71 mmol) of benzyl bromide. The solution was heated at reflux for 3 hours and then concentrated under vacuum. Trituration with ether and filtration provided 763 mg (95%) of the quaternary salt racemic 11α and β-cis-[[2-(acetoxymethyl)cyclohexyl]methyl]-3-(benzyl)-5-(methoxycarbonyl)-1,2,4,6-tetrahydro-3,10b-methanoazepino[4,5-b]indolium bromide with TLC $R_f$ 0.25 (SiO$_2$, 9:1 dichloromethane-methanol, CAS blue green, yellow center). This product was heated at reflux for 4 hours in 30 mL of dry methanol containing 2 mL of triethylamine. After concentration under vacuum, the residue was chromatographed on a 50 g silica gel column, eluting with 1:1 dichloromethane:diethyl ether, to provide 600 mg (90%) of the two diastereomeric title products in a 1:1 parts by weight ratio. Rechromatography under the same conditions provided the racemic 4,1 PARF methyl [3aRS, 4RS, 11bRS]-4-[1RS,2RS]-[2-(acetoxymethyl)cyclohexyl]-3-(benzyl)-1,2,3,3a,4,5-hexahydro-7H-pyrrolo[2,3-d]carbazole-6-carboxylate; TLC $R_f$ 0.27 (SiO$_2$, 1:1 ether:heptane, CAS blue, yellow center) and the racemic 4, 1 PREF methyl [3aRS, 4RS, 11bSR]-4-[1SR,2SR]-[2-(acetoxymethyl)-cyclohexyl]-3-(benzyl)-1,2,3,3a,4,5-hexahydro-7H-pyrrolo[2,3-d]carbazole-6-carboxylate; TLC $R_f$ :.133 (SiO$_2$, 1:1 parts by volume ether: heptane, CAS blue, yellow center).

EXAMPLE 18

Racemic Methyl [3aRS, 4RS, 11bSR]-3-(Benzyl)-4-[1RS, 2RS]-[2-(hydroxymethyl)cyclohexyl]-1,2,3,3a,4,5-hexahydro-7H-pyrrolo[2,3-d]carbazole-6-carboxylate and Racemic Methyl [3aRS, 4RS, 11bSR]-3-(Benzyl)-4-[1SR,2SR]-[2-(hydroxymethyl)cyclohexyl]-1,2,3,3a,4,5-hexahydro-7H-pyrrolo[2,3-d]carbazole-6-carboxylate.

To a solution of 48 mg (2.11 mmol) of sodium in 10 mL of methanol was added 361 mg (0.702 mmol) of a 1:1 mixture of the 4,1 PARF and 4,1PREF diastereomeric acetates, racemic methyl [3aRS, 4RS, 11bSR]-4-[1RS,2RS]-[2-(acetoxymethyl)cyclohexyl]-3-(benzyl)-1,2,3,3a,4,5-hexahydro-7H-pyrrolo[2,3-d]carbazole-6-carboxylate and racemic methyl [3aRS, 4RS, 11bSR]-4-[1SR,2SR]-[2-(acetoxymethyl)cyclohexyl]-3-(benzyl)-1,2,3,3a,4,5-hexahydro-7H-pyrrolo[2,3-d]carbazole-6-carboxylate. After stirring at 20° C. for 3 hours, 10 mL of water was added, followed by 10% ammonium chloride and enough 5% HCl to adjust the pH 7. Extraction with 3×20 mL of dichloromethane, concentration of the extracts under vacuum and chromatography on 20 g of silica gel, eluting with 3:1 dichloromethane:ether gave 156 mg of the 4RS-[1RS, 2RS], (4, 1 PARF) racemic methyl [3aRS, 4RS, 11bSR]-3-(benzyl)-4-[1RS,2RS]-[2-(hydroxymethyl)cyclohexyl]-1,2,3,3a,4,5-hexahydro-7H-pyrrolo[2,3-d]carbazole-6-carboxylate; TLC $R_f$ 0.41 (SiO$_2$, 1:1 ether:pentane, CAS blue); and 135 mg of the 4RS[1SR, 2SR], (4, 1 PREF) racemic methyl [3aRS, 4RS, 11bSR]-3-(benzyl)-4-[1SR, 2SR]-[2-(hydroxymethyl)cyclohexyl]-1,2,3,3a,4,5-hexahydro-7H-pyrrolo[2,3-d]carbazole-6-carboxylate; TLC $R_f$ 0.28 (SiO$_2$, 3:1 dichloromethane:ether, CAS blue) (total products 291 mg, 88%).

EXAMPLE 19

Racemic Methyl [3aRS, 4RS, 11bSR]-3-(Benzyl)-4-[1RS, 2RS]-4-[2-(p-toluenesulfonyloxymethyl)cyclohexyl-1,2,3,3a,4,5-hexahydro-7H-pyrrolo[2,3-d]carbazole-6-carboxylate.

To 138 mg (0.29 mmol) of the 4,1PARF alcohol methyl [3aRS, 4RS, 11bSR]-3-(benzyl)-4-[1RS, 2RS]-[2-(hydroxymethyl)cyclohexyl]-1,2,3,3a,4,5-hexahydro-7H-pyrrolo[2,3-d]carbazole-6-carboxylate in 20 mL of dichloromethane was added 90 μL (0.6 mmol) of triethylamine, followed by 150 mg (0.45 mmol) of p. toluenesulfonic anhydride, added over 2 hours. After 3 hours at 20° C. further 90 μL of triethylamine and 150 mg of p. toluenesulfonic anhydride were added and the mixture stirred 48 hours. Concentration under vacuum and chromatography on 20 g of silica gel, eluting with 1% methanol in dichloromethane, gave 152 mg (82%) of the 4,1 PARF racemic methyl [3aRS, 4RS, 11bSR]-3-(benzyl)-4-[1RS, 2RS]-[2-(p-toluenesulfonyloxymethyl)cyclohexyl-1,2,3,3a,4,5-hexahydro-7H-pyrrolo[2,3-d]carbazole-6-carboxylate.

EXAMPLE 20

Racemic Methyl [3aRS, 4RS, 11bSR]-3-(Benzyl-4-[1SR, 2SR]-4-(2-(p-toluenesulfonyloxymethyl)cyclohexyl-1,2,3,3a,4,5-hexahydro-7H-pyrrolo[2,3-d]carbazole-6-carboxylate.

To the 4,1PREF alcohol methyl [3aRS, 4RS, 11bSR]-3-benzyl-4-[1SR, 2SR]-[2-(hydromethyl)cyclohexyl-1,2,3,3a,4,5-hexahydro-7H-pyrrolo[2,3-d]carbazole-6-carboxylate (273 mg, 0.578 mmol) in 30 mL of dry dichloromethane was added successively 130 μL (0.92 mmol) of triethylamine, 7 mg of 4-dimethylaminopyridine and 283 mg (0.867 mmol) of p. toluenesulfonic anhydride over 2 hours. After 5 hours at 20° C. further 200 μL (1.4 mmol) of triethylamine and 283 mg (0.867 mmol) of p. toluenesulfonic anhydride were added over 30 min. The mixture was stirred for 17 hours and then an excess of 10% sodium carbonate was added. After stirring for 5 min, the phases were separated and the aqueous portion extracted with 3×20 mL of dichloromethane. The dried (MgSO$_4$) and concentrated gummy extracts were leached with 20 mL of ethyl ether and the resulting solution concentrated to 313 ml (86%) of racemic methyl [3aRS, 4RS, 11bSR]-3-(benzyl)-4-[1SR, 2ST]-(2-(p-toluenesulfonyloxymethyl)cyclohexyl-1,2,3,3a,4,5-hexahydro-7H-pyrrolo[2,3-d]carbazole-6-carboxylate. TLC $R_f$ 0.36 (SiO$_2$, 1% methanol in dichloromethane).

EXAMPLE 21

(4aR,8aS,9R,11S) and (4aS,8aR,9S,11R)-15-[1,2,4,4a,5,6,7,8,8a,9,10,11,12 17-Tetradecahydro-11-(methoxycarbonyl)-indolo-(2', 3':6,7,)azonino(1,2,3-bx)isoquinolin-11-yl]vindoline To a cooled solution of 80 mg (0.13 mmol) of racemic methyl [3aRS,4RS,11bSR]-3-(benzyl)-4-[1RS,2;1 RS]-[2-(p. toluenesulfonyloxymethyl)cyclohexyl-1,2,3,3a,4,5-dexahydro-7H-pyrrolo[2,3-d]carbazole-6-carbosylate in 10 mL of dichloromethane, at 0° C., was added 27 µL (0.19 mmol) of dry triethylamine, followed by dropwise addition of 23 µL (0.19 mol) of t. butyl hypochlorite. After stirring for 5 minutes at 0° C. TLC indicated complete reaction of the starting material; TLC $R_f$ 0.26 ($SiO_2$ 1:1 ethyl ether-pentanes, CAS rust-yellow). The mixture was partitioned between 10 mL of water and 3×10 mL of dichloromethane and the dried ($MgSO_4$) organic extracts concentrated under vacuum at 30° C. The residual product was dissolved in 15 mL of dry acetone and cooled at 0° C. After addition of 58 mg (0.11 mmol) of vindline hydrochloride and stirring at 0° C. for 5 minutes, 75 mg (0.54 mmol) of solid silver tetrafluoroborate was added in one portion. After stirring in the dark at 0° C. for 30 minutes, 20 mL of 10% ammonium hydroxide in saturated brine was added. The aqueous layer was extracted with 3×15 mL of dichloromethane and the combined, dried ($MgSO_4$) organic extracts concentrated under vacuum. The residue was dissolved in 10 mL of acetic acid and 70 mg (1.3 mmol) of potassium borohydride added at 20° C. over 30 minutes. After 5 minutes of further stirring the reaction mixture was poured into dichloromethane, ice and excess ammonium hydroxide and, after separation of the strongly basic aqueous solution, it was extracted with 3×20 mL of dichloromethane. The combine organic solutions were dried ($MgSO_4$) and concentrated under vacuum to provide 80 mg of the mixture methyl(5R,7S)-3-(benzyl)-5-[1R,21 R[-[2-(p-toluenesulgonyloxymethyl)cyclohexyl]-1,2,3,4,5,6,7,8-octahydroazonino[5,4-b]indole-7-(15-vindolinyl)-7-carboxylate and its 5S,7R,[1S,2S]diastereomer and recovered vindoline. TLC $R_f$ 0.33 (indole-indolines), 0.19 (vindoline), ($SiO_2$, ethyl acetate). The crude reaction product was dissolved in 50 mL of dry toluene and heated at reflux for 3 hours. The solvent was evaporated under vacuum and the residue triturated with ether and collected by filtration. The white solid was dissolvd in 10 mL of dry methanol, 14 mg of 10% palladium on carbon was added, and the mixture then stirred under an atmosphere of hydrogen for 4 hours. Filtration through Celite 545, with dichloromethane rinses, and concentration gave a gummy product, which was dissolved in 30 mL of dichloromethane and stirred for 3 minutes with 10% aqueous sodium carbonate. Separation of the layers, extraction of the aqueous portion with 3×10 mL of dichloromethane and concentration of the dried ($MgSO_4$) organic solutions gave a product, which was chromatographed on a 3 g silica ged column, eluting with wthyl acetate-ethanol 4:1. The initial fractions contained about 20 mg of the (4aS,8aR,9S,11R)-15-[1,2,4,4a,5,6,7,8,8a,9,10,11,12,17-tetradecahydro-11-(methoxycarbonyl)-indlo(2', 3':6,7,)azonino(1,2,3-bc)isoquinolin-11-yl]vindoline, TLC $R_f$ 0.37 (4:1 ethyl acetate-ethanol, CAS rust), NMR δ0.39, contaminated by some vindoline, TLC $R_f$ 0.48 (4:1 ethyl acetate-ethanol, CAS pink), and were followed by 21 mg (40%) of the (4aR,8aS,9R,11S)-15-[1,2,4,4a,5,6,7,8,8a,9,10,11,12,17-tetradecahydro-11-(methoxycarbonyl)-indlo(2', 3':6,7,)azonino(1,2,3-bc)isoquinolin-11-yl]vindoline, TLC $R_f$ 0.17 (4:1 ethyl acetate-ethanol, CAS rust), NMR δ0.82.

EXAMPLE 22

(4aS,8aR,9R,11S) and (4aR,8aS,9R,11R)-15-[1,2,4,4a,5,6,7,8,8a,9,10,11,12,17-Tetradecahydro-11-(methoxycarbonyl)-indolo(2', 3':6,7,)azonino(1,2,3-bc)isoquinolin-11-yl] vindoline Using the reaction conditions of Example 21, 313 mg (0.50 mmol) of racemic methyl [3aRS,4RS,11bSR]-3-(benzyl)-4-[1SR,21 SR]-[2-(p. toluenesulfonylozymethyl)cyclohexyl-1,2,3,3a,4,5-hexahydro-7H-pyrrolo[2,3d]carbazole-6-carboxylate in 20 mL of dichloromethane was treated with 90 µL (0.75 mmol) of t. butylhypochlorite and 105 µL (0.75 mmol) of triethylamine at 0° C. for 10 minutes. the resultant chloroindolenines product, TLC $R_f$ 0.77, 0.64 (ethyl acetate-dichloromethane 1:1, CAS brown) in 30 mL of dry acetone was allowed to react with 256 mg (0.50 mmol) of vindoline hydrochloride and 293 mg (1.5 mmol) of silver tetrafluoroborate. The resultant crude product was stirred in 25 mL of acetic acid with 275 mg (5.0 mmol) of potassium borohydride. Chromatography on 20 g of silica gel, eluting with ethyl acetate, gae 301 mg (55%) of the mixture Methyl (5R,7S)-3-(benzyl)-5-[1S,2S]-[2-(p-toluenesulfonyloxymetnyl)cyclohexyl]-1,2,3,4,5,6,7,8-octahydroazonino[5,4-b]indole-7-(15-vindlinyl)-7-carboxylate and its 5S,7R,[1R,2R]-diastereomer; TLC $R_f$ 0.39 ($SiO_2$, ethyl acetate, CAS grey-brown). This mixture was heated in 50 mL of dry toluene at reflux for 22 hours. Filtration of the product from ether provided 250 mg of material which was subjected to hydrogenation for 4 hours in 20 mL of methanol with 50 mg of 10% Pd/C. Chromatography of the products on a 6 g silica gel column, eluting first with 4:1 ethyl acetate; ethanol, then with 7:3 ethyl acetate: ethanol containing 0.5% triethylamine gave 51 mg (23% overall) of te (4arR,8aS,9R,11R)-15-[1,2,4,4a,5,6,7,8,8a,9,10,11,12,17-tetradecahydro-11-(methoxycarbonyl)-indolo(2', 3':6,7,)azonino(1,2,3-bc) isoquinolin-11-yl]vindoline; TLC $R_f$ 0.42, (4:1 ethyl acetatea-ethanol, CAS rust brown), NMR δ0.38; and 60 mg (27% overall) of the (4aS,8aR,9R,11S)-15-[1,2,4,4a,;b 5,6,7,8,8a,9,10,11,12,17-tetradecahydro-11-(methoxycarbonyl)-indolo(2',3':6,7,)azonino(1,2,3-bc)isoquinolin-11-yl] vindoline; TLC $R_f$ 0.13 (4:1 ethyl acetate-ethanol, CAS black-brown), NMR δ0.81.

EXAMPLE 23

(4aS,8aR,9R,11l S)-15-[1,2,4,4a,5,6,7,8,8a,9,10,11,12,17-Tetradecahydro-11-(methoxycarbonyl)-indolo(2',3':6,7,)azonino(1,2,3-bc)isoquinolin-11-yl]N-demethyl-N-formylvindoline To a solution of 25 mg (0.031 mmol) of (4aS,8aR,9R,11S)-15-[1,2,4,4a,5,6,7,8,8a,9,10,11,12,17-tetradecahydro-11-(methoxycarbonyl)-indolo(2',3':6,7-,)azonino(1,2,-3-bc)isoquinolin-11-yl]vindoline in 6 mL of sodium distilled tetrahydrofuran at −65° C. was added dropwise, with vigorous stirring, over 3 minutes, a solution of 302 mg of sodium dichromate dihydrate in 1.8 mL of water and 0.206 mL of sulfuric acid, keeping the reaction medium at −55° C. After stirring at −60° to −65° C. for 3 hours the mixture was poured into 4.3 mL of 28% ammonium hydroxide in 24 mL of water, rinsing the reaction flask with 3×5 mL of dichloromethane. Separation of phases, extraction with 4×5 mL of dichloromethane, washing of the combined organic solutions with 10 mL of 5% $Na_2S_2O_2$ solution, drying over $MgSO_4$ and concentration under vacuum gave 23 mg (90%) of the (4aS,8aR,9R,11S)-15-[1,2,4,4a,5,6,7,8,-,8a,9,10,11,12,17-tetradecahydro-11-(methoxycarbonyl)-indolo(2',3':6,7,)azonino(1,2,3-bc)isoquinolin-11-yl]N-demethyl-N-formylvindoline; TLC $R_f$ 0.19 ($SiO_2$, ethyl acetate-ethanol 1:1, CAS blue).

EXAMPLE 24

(4aR,8aS,9R,11S)-15-[1,2,4,4a,5,6,7,8,8a,),10,11,12,17-Tetradecahydro-1-(methoxycarbonyl)-indolo(2',3'-6,7,)azonino (1,2,3,-bc)isoquinolin-11-yl]N-demethyl-N-formylvindoline By the procedure of Example 23, 20 mg (0.024 mmol) of (4aR,8aS,9R,11S)-15;1 -[1,2,4,4a,5,6,7,8-,8a,9,10,11,12,17-tetradecahydro-11-(methoxycarbonyl)-indolo(2',3':6,7,)azinono (1,2,3-bc)isoquinolin-11-yl]vindoline in 6 mL of tetrahydrofuran was oxidized with 242 mg of sodium dichromate dihydrate in 1.5 mL of water and 0.165 mL of sulfuric. The reaction mixture was poured into 3.5 mL of 28% ammonium hydroxide in 20 mL of water and extracted with dichloromethane. After washing of the extracts with 5% $Na_2S_2O_5$ solution and drying ($MgSO_4$), concentration gave 18 mg (89%) of the methyl (4aR,8aS,9R,11S)-15-[ 1,2,4,4a,5,6,7,8,8a,9,10,11,12,17-tetradecahydro-11-(methoxycarbonyl)-indolo(2',3':6,7,)azonino(1,2,3-bc)isoquinolin-11-yl]N-demethyl-N-formylvindline; TLC Rf 0.22 1 ($SiO_2$, ethyl acetate-ethanol, 1:1, CAS purple).

EXAMPLE 25 cis-Bicyclo[3.3.0]-octane-3-one

A solution of the cis-bicyclo[3.3..0]oct-6-ene-3-one (6.2 g 0.05 mol) in 150 mL of ethyl acetate containing 0.50 g of 10% Pd/C was hydrogenated at 25 psi for 1½ hours. The catalyst was removed by filtering through Celite and the solvent evaporated to give 6.5 g of cis-bicyclo[3.3.0]-octane-3-one (100%). TLC ($SiO_2$, $CH_2Cl_2$) $R_f$=0.35 ($I_2$, brown).

EXAMPLE 26

(cis-rac)-Hexahydro-cyclopenta[c]pyran-3-(1H)-one

The cis-bicyclo [3.3.0] octanone (7.0 g, 0.0566 mol) was stirred with $NaHCO_3$ (41.1 g, 0.489 mol) and m. chloroperoxybenzoic acid (22.1 g, 0.128 mol) in 250 mL of dichloromethane at 20° C. for 24 hours. Then 200 mL of 10% $Na_2S_2O_3$ was added and the mixture stirred for 20 minutes when two phases appeared. The organic phase was separated and washed three times with 10% $Na_2CO_3$, 3 times with water and finally with brine. The organic extracts were dried over $MgSO_4$ and the solvent evaporated. The crude product was chromatographed on silica gel with $CH_2Cl_2$ to afford 6.24 g of (cis-rac)-hexahydrocyclopenta[c]pyran-3-(1H)-one (79%). TLC ($SiO_2$, $CH_2Cl_2$) $R_f$=0.25 ($I_2$, brown).

EXAMPLE 27

(cis-rac)-Hexahydro-1H-cyclopenta[c]pyran-3-ol

A solution of 2.1 g (0.0143 mol) of lactone in 50 mL of $CH_2Cl_2$ was cooled to −78° C. A 1M solution of diisobutylaluminum hydride in $CH_2Cl_2$ (16 mL, 0.016 mL) was added dropwised and the mixture allowed to slowly warm to 0° C. TLC showed the reaction to be complete ater 1 hour. The mixture was acidified with 1M HCl to pH 2. The aqueous phase was extracted three times with ether. The combined organic layers were washed with 5% $NaHCO_3$ and brine. Drying over $MgSO_4$ and concentration of the organic extracts gave 1.76 g of (cis-rac)-hexahydro-1H-cyclopenta[c]pyran-3-ol (87%). TLC ($SiO_2$/$Et_2O$) $R_f$=0.55 (CAS, dark brown with heat).

EXAMPLE 28

(cis-rac)-2-(1,3-Dithiolan-2-ylmethyl)cyclopentanemethanol

The (cis-rac)-hexahydro-1H-cyclopenta[c]pyran-3-ol (2.73 g, 0.0192 mol) was dissolved in 5 equivalents of dithioethane (8.1 mL, 0.096 mol) and cooled to 0° C. 12N HCl (1.2 equivalents) was added dropwise to the reaction mixture. The mixture was allowed to warm to 20° C. and stirred for 2 hours. Then 3.6 equiv. of concentrated HCl was added and the mixture stirred for an additional 45 minutes. The reaction mixture was poured into ice water and extracted three times with $CH_2Cl_2$. The combined organic layers were washed with 5% $NaHCO_3$, brine, and dried over $MgSO_4$. The solvent was evaporated and the product was chromatographed on silica gel with $CH_2Cl_2$, followed by ether, to yield 3.3 g of (cis-rac)-2-(1,3-dithiolan-2-ylmethyl)cyclopentanemethanol(79%). TLC ($SiO_2$, ether) $R_f$=0.54 (CAS brown when heated).

EXAMPLE 29

(cis-rac)-2-(1,3-Dithiolan-2-ylmetyl)cyclopentanemethanol acetate

The (cis-rac)-2-(1,3-dithiolan-2-ylmethyl)cyclopentanemethanol(3.3 g, 0.015 mol) and pyridine (1.46 mL, 0.018 mol) were dissolved in 50 mL of $CH_2Cl_2$ and the solution cooled to 0° C. Acetyl chloride (1.29 mL, 0.018 mol) was added dropwise at 0° C. and then the mixture was allowed to warm to 20° C. After 0.5 hours the reaction was complete as seen by TLC. The mixture was washed with water, 1M HCl, 5% $NaHCO_3$, brine, and dried over $MgSO_4$. The solvent was evaporated and the crude compound chromatographed with $CH_2Cl_2$ on silica gel to give 3.70 g of (cis-rac)-2-(1,3-dithiolan-2-ylmethyl)cyclopentanemethanol acetate (95%). TLC ($SiO_2CH_2Cl_2$) $R_f$=0.31 (CAS, orange when heated).

EXAMPLE 30

(cis-rac)-2-[(Acetyloxy[methyl]cyclopentaneacetaldehyde

Mercuric oxide [HgO] (3.99 g, 0.0184 mol) was added to 30 mL of 15% aqueous tetrahydrofuran, followed by 9 mL of 35% $HBF_4$ in ether. The (cis-rac)-2-(1,3-dithiolan-2-ylmethyl)cyclopentanemethanol acetate, (1.77 g, 1.72 mmol) in tetrahydrofuran, was added and the mixture stirred for 5 minutes. Dilution with dichloromethane until a white precipitate formed and filtration through Celite, washing with dichloromethane, gave an organic solution, which was washed with 10% NaI, 5% $NaHCO_3$, and brine. The organic phase was dried over $MgSO_4$ and concentrated. Chromatography on silica gel with hexane/$Et_2O$, 1:1, gave 1.33 g of (cis-rac)-2-[(acetyloxy[methyl]cyclopentaneacetaldehyde (78%). TLC ($SiO_2$, hexane/$Et_2O$ 1:2) $R_f$=0.35 (CAS, brown when heated).

EXAMPLE 31

[3aRS,4RS,4(1RS,2RS),11bSR]-4-[2-(Acetyloxymethyl)cyclopenty-1]-2,3,3a,4,5,7-hexahydro-3-(phenylmethyl)-1H-pyrrolo[2,3,-d]carbazole-6-carboxylic acid methyl ester and
[3aRS,4RS,4(1SR,2SR),11bSR]-4-[2-(Acetyloxy)methyl]cyclopentyl]-2,3,3a,4,5,7-hexahydro-3-(phenylmethyl)-1H-pyrrolo[2,3-d]carbazole-6-carboxylic acid methyl ester.

The indoloazepine methyl 1,2,3,4,5,6-hexahydroazepino(4,5-b)indole-5-carboxylate (1.81 g, 7.41 mmol) was dissolved in 35 mL of dry dichloromethane and the (cis-rac)-2-[(acetyloxy[methyl]cyclopentaneacetaldehyde (1.65 g, 8.97 mmol) was added. The solution was stirred overnight at 20° C. TLC (SiO$_2$, 10% methanol/CH$_2$Cl$_2$) of the mixture showed the formation of two produces (R$_f$ 0.51 and 0.74, CAS, blue). The reaction mixture was concentrated and immediately dissolved in 35 mL of CHCl$_3$. To the solution was added benzyl bromide (2.2 mL, 18.5 mmol) and then the mixture was heated at reflux until TLC showed complete formation of the salt (about 4 hours). The solvent was evaporated under vacuum and the residual salt was triturated with ether and filtered. The solid was then dissolved in 30 mL of dry methanol and 2 mL of triethylamine and the solution heated at reflux overnight. The methanol was evaporated and the residue was chromatographed (SiO$_2$, 2:1 ether/hexane) to give 3.1 g (84%) of a mixture of 2 isomers formed in a 1:1 ratio. These two isomers were [3aRS,4RS,4(1RS,2RS),11bSR]-4L -[2-(acetyloxy) methyl]cyclopentyl]-2,3,3a,4,5,7-hexahydro-3-(phenylmethyl)-1H-pyrrolo[2,3-d]carbazole-6-carboxylic acid methyl ester and [3aRS,4RS,4(1SR,2SR),11bSR]-4-[2-(acetyloxy) methyl]cyclopentyl]-2,3,3a,4,5,7-hexahydro-3-(phenylmethyl)-1H-pyrrolo[2,3-d]carbozole-6-carboxylic acid methyl ester.

Data for less polar isomer [3aRS,4RS,4(1RS,2RS),11bSR]-4-(2-(acetyloxy) methyl]cyclopentyl]-2,3,3a,4,5,7-hexahydro-3-(Phenylmethyl)-1H-pyrrolo[2,3-d]carbazole-6-carboxylic acid methyl ester. TLC (SiO$_2$, 2:1 ether/hexane) R$_f$ 0.38 (CAS, blue).

Data for more polar isomer [3aRS,4RS,4(1SR,2SR),11bSR]-4-[2-(acetyloxy)methyl]cyclopentyl]-2,3,3a,4,5,7-hexahydro-3-(phenylmethyl)-1H-pyrrolo[2,3-d]carbazole-6-carboxylic acid methyl ester: TLC (SiO$_2$, 2:1 ether/hexane) R$_f$ 0.27 (CAS, blue).

EXAMPLE 32

[3aRS,4RS,4(1RS,2RS),11bSR]-2,3a,4,5,7-hexahydro-4-[2-(hydroxymethyl)cyclopentyl]-3-(phenylmethyl)-1H-pyrrolo [2,3-d]carbazole-6-carboxylic acid methyl ester and
[3aRS,4RS,4(1SR,2SR,11bSR]2,3a,4,5,7-hexahydro-4-[2-(hydroxymethyl)cyclophentyl]-3-(phenylmethyl)-1H-pyrrolo [2,3-d]carbazole-6-carboxylic acid methyl ester The mixture of the two isomers prepared in Example 31 (3.0 g, 6 mmol) was dissolved in 100 mL of methanol and K$_2$CO$_3$ (1.66 L g, 12 mmol) was added. A few drops of water were added and the solution was heated at reflux for 0.5 hours. TLC (SiO$_2$, 1:1 ether/hexane) showed the formation of two products (R$_f$ 0.20 and 0.49, CAS, blue). The reaction mixture was neutralized to pH 7 with 1% HCl and the methanol was evaporated. The residue was then dissolved in dichloromethane and washed with water and brine. The organic phase was dried over Na$_2$SO$_4$ and the solvent evaporated. The two isomers were separated by chromatography (SiO$_2$, 1:1 ether/hexane) to give 51.5% of the less polar isomer [3aRS,4RS,4(1RS,2RS),11 bSR]-2,3a,4,5,7-hexahydro-4-[2-(hydroxymethyl)cyclopentyl]-3-(phenylmethyl)-1H-pyrrolo [2,3-]carbazole-6-carboxylic acid methyl ester and 46% of the more polar isomer [3aRS,4RS,4(1SR,2SR),11bSR]-2,3a,4,5,7-hexahydro-4-[2-(hydroxymethyl)cyclopentyl]-3-(phenylmethyl)-1H-pyrrolo [2,3-α]carbazole-6-carboxylic acid methyl ester with the less polar isomer having TLC (SiO$_2$, 1:1 ether/hexane) R$_f$ 0.49 (CAS, blue) and the more polar isomer having TLC (SiO$_2$, 1:1 ether/hexane) R$_f$ 0.20 (CAS, blue).

EXAMPLE 33

[3aRS,4RS,4(1RS,2RS),11bSR]-2,3a,4,5,7-hexahydro-4-[2-[[[(4-methylphenyl)sulfonyl]oxy]methyl]cyclophenyl]-3-(phenylmethyl)-1H-pyrrolo[2,3-d]carbazole-6-carboxylic acid methyl ester and
[3aRS,4RS,4(1SR,2SR),11bSR]-2,3a,4,5,7-hexahydro-4-[2-[[[(4-methylphenyl)sulfonyl]oxy]methyl]cyclopentyl]-3-(phenylmethyl)-1H-pyrrolo[2,3-d]carbazole-6-carboxylic acid methyl ester Each of the isomers prepared in Exampe 32 were separately converted to the title product by the following procedure: To 30 mL of dichloromethane was added either the isomer (3RS,4l RS,4(1RS,2RS),11bSR]-2,3a,4,5,7-hexahydro-4-[2-(hydroxymethyl)cyclopentyl]-3-(phenylmethyl)-1H-pyrrolo[2,3-d]-carbazole-6-carboxylic acid methyl ester or the isomer [3aRS,4l RS,4(1SR,2SR),11bSR]-2,3a,4,5,7-hexahydro-4-[2-(hydroxymethyl)cyclopentyl]-3-(phenylmethyl)-1H-pyrrolo[2,3-d]-carbazole-6-carboxylic acid methyl ester (300 mg, 0.655 mmol) and triethylamine (0.14 mL, 0.098 mmol). The reaction mixture was cooled to 0° C. and p-toluenesulfonic anhydride (0.32 g, 0.98 mmol), dissolved in 10 mL of dichloromethane, was added dropwise to the mixture. the mixture was allowed to warm slowly to 20° C. and stirred overnight at 20° C. The reaction mixture was then washed with 10% Na$_2$CO$_3$ in brine, dried over Na$_2$SO$_4$ and the solvent evaporated. The crude product was chromatographed on silica gel with ether/hexane, 3:1, for the more polar isomer and with 2:1 ether/hexane for the less polar isomer, to yield 0.363 g (91%) and 0.295 g (74%) respectively. The less polar isomer was [3aRS,4RS,4(1RS,2RS),11bSR]-2,3a,4,5,7-hexahydro-4-[2-[[[(4-methylphenyl)sulfonyl]oxy]methyl]-cyclopentyl]-3-(phenylmethyl)-1H-pyrrolo[2,3-α]carbazole-6-carboxylic acid methyl ester which had TLC (SiO$_2$, 1:1 ether/hexane) R$_f$ 0.70 (CAS, blue); and the more polar isomer was [3aRS,4RS,4(1SR,2SR),11bSR]-2,3a,4,5,7-hexahydro-4-[2-[[[(4-methylphenyl)sulfonyl]oxy]methyl]-cyclopentyl]-3-(phenylmethyl)-1H-pyrrolo[2,3-α]carbazole-6-carboxylic acid methyl ester which had TLC (SiO$_2$, 1:1 ether/hexane) R$_f$0.69 (CAS, blue).

EXAMPLE 34

Diastereomeric [2R,3R,4R,5R,12S,15[5R(S),5(-1R(S),2R(S)),7S,(R)],19R]-4-(acetyloxy)-6,7-didehydro-15-[1,2,3,4,5,6,7,8-octahydro-7-(methoxycarbonyl)-5-[2-[[[(4-methylphenyl)sulfonyl]oxy]cyclopentyl]-3-(phenylmethyl)azonino[5,4-b]indol-7-yl]-3-hydroxy-16- methoxy-1-methylaspidospermidine-3-carboxylic acid methyl esters

The less polar tosylate [3aRS,4RS,4(1RS,2RS),-11bSR]-2,3a,4,5,7-hexahydro-4-[2-[[[(4-methylphenyl)-sulfonyl]oxy]methyl]cyclopentyl]-3-(phenylmethyl)-1H-pyrrolo[2,3-α]carbazole-6-carboxylic acid methyl ester (300 mg, 0.49 mmol) was dissolved in 30 mL of dry dichloromethane and triethylamine (0.09 mL, 0.65 mmol). The solution was then cooled to 0° C. and t-butyl hypochlorite (0.076 mL, 0.65 mmol) was added dropwise. After 5 minutes TLC on silica gel showed chloro product [3aRS,4RS,4(1RS,2RS),6ξ,11bSR]-6-chloro-2,3a,4,5,6-hexahydro-4-[2-[[[(4-methylphenyl)-sulfonyl]oxy]methyl]cyclopentyl]-3-(phenylmethyl)-1H-pyrrolo[2,3-d]carbazole-6-carboxylic acid methyl ester which turned brown with CAS spray. The reaction mixture was washed with water and brine, dried over $Na_2SO_4$ and the solvent evaporated to yield a white foam, which was used immediately for the next reaction.

The [3aRS,4RS,4(1RS,2RS),6ξ,11bSR]-6-chloro--2,3a,4,5,6-hexahydro-4-[2-[[[(4-methylphenyl)-sulfonyl]oxy]methyl]cyclopentyl]-3-(phenylmethyl)-1H-pyrrolo[2,3-d]carbazole-6-carboxylic acid methyl esters were dissolved in 15 mL of dry acetone and vindoline (0.205 g, 0.45 mmol) was added. The solution was cooled to 0° C. and tetrafluoroboric acid diethyl ether complex (0.129 mL, 0.75 mmol) was added dropwise. After 5 minutes, $AgBF_4$(0.194 g, 0.99 mmol) in 5 mL of acetone, was syringed into the reaction mixture. The reaction was complete after 10 minutes. The mixture was poured into 10% $K_2CO_3$ and ice and the aqueous layer was extracted three times with dichloromethane. The combined organic phases were washed with brine, dried over $Na_2SO_4$, and the solvent evaporated. The resulting crude [2R,3R,4R,5R,12S,15[3aR(S),4R(S),4(1R(S),2R(S)),6S(R)]19R]-4-(acetyloxy)-6,7-didehydro-5-[2,3,3a,4,5,6-dexahydro-6(methyoxycarbonyl)-4-[2-[[[(4-methylphenyl)-sulfonyl]oxy]methyl]-cyclopentyl]-3-(phenylmethyl)-1H-pyrrolo-[2,3-d]carbazole-6-yl]-3-hydroxy-16-methoxy-1-methyl-aspidospermidine-3-carboxylic acid methyl esters were then dissolved in 15 mL of acetic acid and potassium borohydride (0.27 g, 4.98 mmol) was added in portions. The mixture was stirred for another 10 minutes and then poured into 10% $K_2CO_3$ and ice (pH 9–10). The aqueous phase was extracted three times with dichloromethane and the combined organic layers were washed with water, brine and dried over $Na_2SO_4$. The solvent was evaporated to give the crude [2R,3R,4R,5R,12S,15[5R(S),5(1R(S),2R(S)),7S(R)],19R]-4-(acetyloxy)-6,7-didehydro-15-[1,2,3,4,5,6,7,8-octahydro-7-(methoxycarbonyl)-5-[2-[[D4-methylphenyl)sulfonyl]oxy]cyclopentyl]-3-(phenylmethyl)azonino[5,4-b]indol-7-yl]-3-hydroxy-16-methoxy-1-methylaspidospermidine-3-carboxylic acid methyl esters, some of which had already cyclized to the quaternary ammonium salt. TLC (ethyl acetate) showed the coupling products $R_f$ 0.45, and their cyclization products $R_f$ 0.0 (CAS, brown). The compounds were chromatographed on silica gel, eluting first with ethyl acetate, followed by 9:1 $CH_2Cl_2$/methanol, to isolate the quaternary salts [4aR(S),7aS(R),-8R(S),10S(R)]-15-(3-benzyl)-2,4,4a,5,6,7-,7a,8,9,10,11,16-dodecahydro-10-(methoxycarbonyl)-1H-indolo(2′,3′:6,7)azonino(1,2,3-bc)-2-pyrindin-10-yl]vindoline-4-methylbenzene sulfonate (1:1) salt (48% total based on 0.9 equiv. of vindoline and then the amino tosylate esters [2R,3R,4R,5R,12S,15[5R(S),5(1R(S),2R-(S)),7S(R)],19R]-4-(acetyloxy)-6,7-didehydro-15-[1,2,3,4,5,6,7,8-octahydro-7-(methoxycarbonyl)-5-[2-[[[(4-methylphenyl)sulfonyl]oxy]cyclopentyl]-3-(phenylmethyl)azonino[5,4-b]indol-7-yl]-3-hydroxy-16-methoxy-1-methylaspidospermidine-3-carboxylic acid methyl ester.

EXAMPLE 35

(4aR,7aS,8R,10S)-15-[2,4a,5,6,7a,8,8a,9,10,11,16-dodecahydro-10-(methoxycarbonyl)-1H-indolo(2′,3′:6,7,)azonino(1,2,3-bc)-2-pyrindin-10-yl]vindoline The diastereomeric compounds, [2R,3R,4R,5R,12S,15[5R(S),5(1S(R),2S(R)),7(S)R],19R]--4-(acetyloxy)-6,7-didehydro-15-]1,2,3,4,5,6,7,8-octahydro-7-(methoxycarbonyl)-5-[2-[[[(4-methylphenyl)sulfonyl]oxy]-cyclopentyl]-3-(phenylmethyl)azonino[5,4-b]indole-7-yl]-3-hydroxy-16-methoxy-1-methylaspidospermidine-3-carboxylic acid methyl esters (163 mg, 0.15 mmol) were dissolved in 7 mL of dry THF and heated at reflux for 2 hours, to produce the quaternary salt i.e. [4aR(S),7aS(R),8R(S),10S(R)]-15-[(3-benzyl)-2,4-,4a,5,6,7,7a,8,9,10,11,16-dodecahydro-10-(methoxycarbonyl)-1H-indolo(2′,3′:6,7)azonino(1,2,3-bc)-2-pyrindin-10-yl)]vindoline-4-methylbenzene sulfonate (1:1) salt. The solvent was then evaporated under vacuum and the residue dissolved in 15 mL of dry methanol. To the solution was added 15 mg of 10% Pd/C and the mixture was stirred under hydrogen for 2 hours for debenzylation. The mixture was filtered through Celite, the residue washed several times with dichloromethane and the combined filtrate partitioned between 10% $K_2CO_3$ and dichloromethane. The organic extracts were washed with brine, dried over $Na_2SO_4$ and concentrated, to yield (4aS,7aR,8S,10R)-15-[2,4,4a,5,6,7-,7a,8,9,10,11,16-dodecahydro-10-(methoxycarbonyl9-1H-indolo-(2′,3′:6,7,)azonino(1,2,3,-bc)-2-pyrindin-10-yl]vindoline with TLC $R_f$ 0.46 ($SiO_2$, 10% methanol/$CH_2Cl_2$) and (4aR,7aS,8R,10S)-15-[2,4,4a,5,6,7-,7a,8,9,10,11,16-dodecahydro-10-(methoxycarbonyl9-1H-indolo(2′,3′:6,7,)azonino(1,2,3-bc)-2-pyrindin-10-yl]vindoline with TLC 0.37 ($SiO_2$, 10% methanol/$CH_2Cl_2$). These isomers were separated by column chromatography on silica gel, eluting first with 5% methanol/$CH_2Cl_2$ then with 10% methanol/$CH_2Cl_2$ to yield 47.7 mg of (4aR,7aS,8R,10S)-15-[2,4,4a,5,6,7,7a,-8,9,10,11,16-[2,4,4a,-5,6,7,7a,8,9,10,11,16-dodecahydro-10-(methoxycarbonyl)-1H-indolo(2′,3′:6,7-,)azonino(1,2,3-bc)-2-pyrindin-10-yl]vindoline (39% yield). TLC ($SiO_2$, 10% methanol/$CH_2Cl_2$) $R_f$ 0.37 (CAS, brown).

EXAMPLE 36

[2R,3R,4R,5R,12S,15[5S,5(1SR,2SR),7S],19R]-4-(acetyloxy)-6,7-didehydro-15-[1,2,3,4,5,6,7,8-octahydro-7-(methoxycarbonyl)-5-[2-[[[(4-methylphenyl)sulfonyl]oxy]cyclopentyl]-3-(phenylmethyl)azonino[5,4-b]indol-7-yl]-3-hydroxy-16-methoxy-1-methylaspidospermidine-3-carboxylic acid methyl ester By the procedure of Example 34 first paragraph, the more polar tosylate [3aRS,4Rs,4(1SR,2SR),11bSR]-2,3a,4,5,7-hexahydro-4-[2-[[[(4-methylphenyl)sulfonyl]oxy]methyl]cyclopentyl]-3-(phenylmethyl)-1H-pyrrolo[2,3-d]carbazole-6-carboxylic acid methyl ester was converted to the chloride: [3aRS,4RS,4(1SR,2SR)-,6ξ,11bSR]-6-chloro-2,3a,4,5,6-hexahydro-4-[2-[[[(4-methylphenyl)sulfonyl]oxy]methyl]cyclopentyl]-3-

(phenylmethyl)-1H-pyrrolo[2,3-d]carbazole-6-carboxylic acid methyl esters. These halides were condensed with vindoline by the procedure of Example 35 to produce the condensation products: ]2R,3R,4R,5R,12S,15[3aR,4R,4(1S,2S),6S]19R]-4-(acetyloxy)-6,7-didehydro-5-[2,3,3a,4,5,6-hexahydro-6-(methoxycarbonyl)-4-[2-[[[(4-methylphenyl)sulfonyl]oxy]methyl]cyclopentyl]-3-(phenylmethyl9-1H-pyrrolo[2,3-d]carbazole-6-yl]-3-hydroxy-16-methoxy-1-methylaspidospermidine-3-carboxylic acid methyl ester and [2R,3R,4R,5R,12S,15[3aS,4S,4(1R,2R),6R]19S]-4-(acetyloxy)-6,7-didehydro-5-[2,3,3a,4,5,6-hexahydro-6-(methoxycarbonyl9-4-[2-[[[(4-methylphenyl)sulfonyl]oxy]methyl]cyclopentyl]-3-(phenylmethyl9-1H-pyrrolo[2,3-d]-carbazole-6-yl]-3-hydroxy-16-methoxy-1-methylaspidospermidine-3-carboxylic acid methyl ester. This diastereomeric mixture was converted to the tosylates [2R,3R,4R,5R,12S,15[5R(S),5(1S(R),2S(R)),7S(R)],1-9R]-4-(acetyloxy)-6,7-didehydro-15-[1,2,3,4,5,6,7,8-octahydro-7-(methoxycarbonyl)-5-[2-[[[(4-methylphenyl)-sulfonyl]oxy]cyclo-pentyl]-3-(phenylmethyl)azonino[5,4-b]indol-7-yl]-3-hydroxy-16-methoxy-1-methylaspidospermidine-3-carboxylic acid methyl ester by the procedure of the second paragraph of Example 34.

EXAMPLE 37

(4aS,7aR,8R,10S)-15-[2,4,4a,5,6,7,7a,8,9,10,11,16-dodecahydro-10-(methoxycarbonyl)-1H-indolo(2',3':6,7,)azonino(1,2,3-bc)-2-pyrindin-10-yl]vindoline By the procedure of Example 35, [2R,3R,4R,5R,12S,15[5R(S),5(1S(R),2S(R)),7S(R)],19R]--4-(acetyloxy)-6,7-didehydro-15-[1,2,3,4,5,6,7,8-octahydro-7-(methoxycarbonyl)-5-[2-[[[(4-methylphenyl)sulfonyl]oxy]cyclopentyl]-3-(phenylmethyl)azonino[5,4-b]indol-7-yl]-3-hydroxy-16-methoxy-1-methylaspidospermidine-3-carboxylic acid methyl ester was converted to the product (4aS,7aR,8R,10S)-15-[2,4,4a,5,6,7-,7a,8,8a,9,10,11,16-dodecahydro-10-(methoxycarbonyl)-1H-indolo(2',3':6,7)azonino(1,2,3-bc)-2-pyrindin-10-yl]vindoline via the intermediate (4aS(R),7-aR(S),8S(R),10R(S)-15-[3-benzyl-2,4,4a,5,6,7-,7a,8,9,10,11,16-dodecahydro-10-(methoxycarbonyl)-1H-indolo(2',3':6,7)azonino(1,2,3-bc)-2-pyrindin-10-yl]vindoline. The product had the following properties; TLC SiO2, ether/acetone/triethylamine 100:30:3) R$_f$ 0.10 (CAS, brown).

I claim:

1. A compound of the formula:

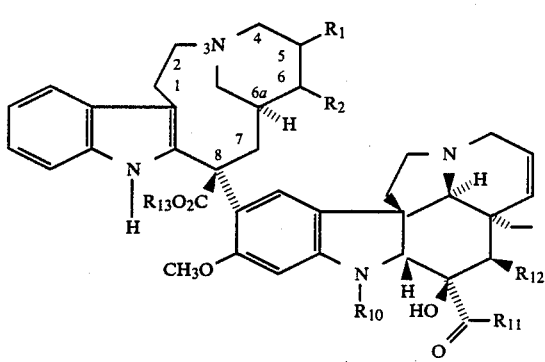

I wherein R$_1$ and R$_2$ are in a cis relationship and taken together form —CH$_2$—(CH$_2$)$_n$—CH$_2$; or R$_1$ and R$_2$ taken together with their attached carbon atoms form a benzene ring; R$_{10}$ is formyl or methyl; n is an integer from 0 to 3; R$_{11}$ is lower alkoxy containing from 1 to 7 carbon atoms, —NR$_3$R$_3$'or

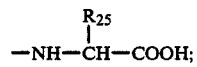

R$_{12}$ is lower alkanoyloxy containing from 1 to 7 carbon atoms or hydroxy; R$_{13}$ is lower alkyl containing from 1 to 7 carbon atoms, R$_3$ and R$_3$' are hydrogen or lower alkyl containing from 1 to 7 carbon atoms; and R$_{25}$ is that portion of a natural a-amino acid which distinguishes one natural a-amino acid from another; its corresponding diastereoisomer having the reverse stereoconfiguration at the 6a and 8 positions or mixtures thereof.

2. The compound of claim 1 wherein the compound has the same absolute configuration as shown.

3. The compound of claim 2 wherein R$_{10}$ is methyl.

4. The compound of claim 3 wherein said R$_1$ and R$_2$ taken together with their attached carbon atoms form a benzene ring.

5. The compound of claim 4 wherein said compound is (9R,11S)-15-[1,2,4,9,10,11,12,17-octahydro-11-(methoxycarbonyl)-indolo(2',3':6,7)azonino(1,2,3-bc)isoquinolin-11-yl]vindoline.

6. The compound of claim 3 wherein R$_1$ and R$_2$ taken together form —CH$_2$—(CH$_2$)$_n$—CH$_2$ and n is above.

7. The compound of claim 6 wherein said compound is (4aS,8aR,9R,11S)-15-[1,2,4,4a,5,6,7,8-,8a,9,10,11,12,17-tetradecahydro-11-(methoxycarbonyl)-indolo-(2',3':6,7)azonino(1,2,3-bc)isoquinolin-11-yl]vindoline.

8. The compound of claim 6 wherein said compound is (4aR,8aS,9S,11R)-15-[1,2,4,4a,5,6,7,8-,8a,9,10,11,12,17-tetradecahydro-11-(methoxycarbonyl)-indolo-(2',3':6,7)azonino(1,2,3-b)isoquinoline-11-yl]vindoline.

9. The compound of claim 6 wherein said compound is (4aR,8aS,9R,11S)-15-[1,2,4,4a,5,6,7,8,-8a,9,10,11,12,17-tetradecahydro-11-(methoxycarbonyl)-indolo-(2',3':6,7)azonino(1,2,3-bc)isoquinolin-11-yl]vindoline.

10. The compound of claim 6 wherein said compound is (4aS,8aR,9S,11R)-15-[1,2,4,4a,5,6,7,8-,8a,9,10,11,12,17-tetradecahydro-11(methoxycarbonyl9-indolo-(2',3':6,7)azonino(1,2,3-bc)isoquinolin-11-yl)vindoline.

11. The compound of claim 6 wherein said compound is (4aS,7aR,8R,10S)-15-[2,4,4a,5,6,7,7a,8,9,10,11,16-dodecahydro-10-(methoxycarbonyl)-1H-indolo(2',3':6,7,)azonino(1,2,3-bc)-2-pyrindin-10-yl]vindoline.

12. The compound of claim 6 wherein said compound is (4aR,7aS,8R,10S)-15-[2,4,4a,5,6,7a,8a,9,10,11,16-dodecahydro-10-(methoxycarbonyl)-1H-indolo(2',3':6,7,)azonino(1,2,3-bc)-2-pyrindin-10-yl]vindoline.

13. The compound of claim 2 wherein R$_{10}$ is formyl.

14. The compound of claim 13 wherein said R$_1$ and R$_2$ taken together form a phenyl ring.

15. The compound of claim 14 wherein said compound is (9R,11S)-15-[1,2,4,9,10,11,12,17-octahydro-11-(methoxycarbonyl)-indolo(2',3':6,7)azonino(1,2,3-bc)isoquinolin-11-yl]N-demethyl-N-formylvindoline.

16. The compound of claim 13 wherein $R_1$ and $R_2$ taken together form —CH$_2$—(CH$_2$)$_n$—CH$_2$.

17. The compound of claim 14 wherein said compound is (4aS,8aR,9R,11S)-15-[1,2,4,4a,5,6,7,8,8a,9,10,11,12,17-tetradecahydro-11-(methoxycarbonyl9-indolo(2',3':6,7)azonino(1,2,3-bc)isoquinolin-11-yl]N-demethyl-N-formylvindoline.

18. The compound of claim 16 wherein said compound is (4aR,8aS,9R,11S)-15-[1,2,4,4a,5,6,7,8,8a,9,10,11,12,17-tetradecahydro-11-(methoxycarbonyl)-indolo(2',3':6,7,)azonino(1,2,3-bc)isoquinolin-11-yl]N-demethyl-N-formylvindoline.

19. The compound of claim 1 wherein said compound has the opposite configuration at the 6a and 8 positions from that shown.

20. The compound of claim 19 wherein $R_1$ and $R_2$ taken together with their attached carbon atom form a benzene ring.

21. The compound of claim 19 wherein said compound is (9,11R)-15-[1,2,4,9,10,11,12,17-octahydro-11-(methoxycarbonyl)-indolo(2',3':6,7)azonino(1,2,3-bc)isoquinolin-11-yl]vindoline.

22. The compound of claim 19 wherein $R_1$ and $R_2$ taken together for —CH$_2$(—CH$_2$)$_n$—CH$_2$ and n is as above.

23. The compound of claim 22 wherein said compound is (4aS,8aR,9S,11R)-15-[1,2,4a,5,6,7,8,8a,9,10,11,12,17-tetradecahydro-11-(methoxycarbonyl)-indolo(2',3':6,7)azonino(1,2,3-bc)isoquinolin-11-yl]vindoline.

24. The compound of claim 22 wherein said compound is (4aR,8aS,9S,11R)-15-[1,2,4,4a,5,6,7,8,8a,9,10,11,12,17-tetradecahydro-11-(methoxycarbonyl)-indolo(2',3':6,7)azonino(1,2,3-bc)isoquinolin-11-yl]vindoline.

25. The compound of claim 22 wherein said compound is (4aS,7aR,8S,10R)-15-[2,4,4a,5,6,7,7a,8,9,10,11,16,dodecahydro-10-(methoxycarbonyl)-1H-indolo(2',3':6,7,)azonino(1,2,3-bc)-2-pyrindin-10-yl]vindoline.

26. The compound of claim 22 wherein said compound is (4aR,7aS,8S,10R)-15-[2,4a,5,6,7a,8,8a,9,10,11-16-dodecahydro-10-(methoxycarbonyl)-1H-indolo(2',3':6,7,)azonino(1,2,3-bc)-2-pyrindin-10-yl]vindoline.

27. A compound of the formula:

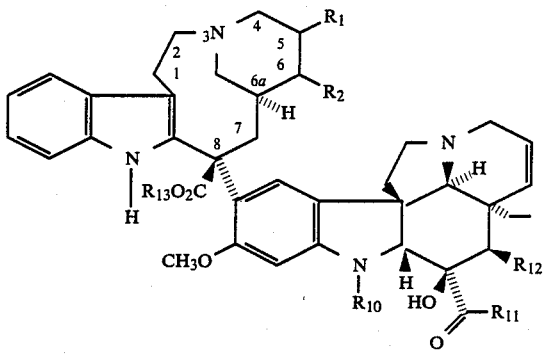

wherein $R_1$ and $R_2$ are in a cis relationship and taken together form —CH$_2$—(CH$_2$)$_n$—CH$_2$; or $R_1$ and $R_2$ taken together with their attached carbon atoms form a benzene ring; n is an integer from 0 to 3; $R_{10}$ if formyl or methyl; $R_{11}$ is lower alkoxy containing from 1 to 7, carbon atoms —NR$_3$R$_3'$ or

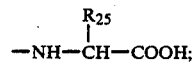

$R_{12}$ is lower alkanoyloxy containing from 1 to 7 carbon atoms or hydroxy; $R_{13}$ is lower alkyl containing from 1 to 7 carbon atoms, $R_3$ and $R_3'$ are hydrogen or lower alkyl containing from 1 to 7 carbon atoms; $R_{25}$ is that portion of a natural a-amino acid which distinguishes one natural a-amino acid from another; and $R_5$ is an amino protecting group; its corresponding diastereoimer having the reverse stereo-configuration at the 6a and 8 positions or mixtures thereof.

28. The compound of claim 27 wherein $R_1$ and $R_2$ taken together with their attached carbon atoms form a benzene ring.

29. The compound of claim 27 wherein $R_1$ and $R_2$ taken together form —CH$_2$(CH$_2$)$_n$—CH$_2$ and n is as above.

30. The compound of claim 29 wherein said compound is (4aR,7aS,8R,10S)-15-[3-benzyl-2,4,4a,5,6,7,7a,8,9,10,11,16-dodecahydro-10-(methoxycarbonyl)-1H-indolo(2',3':6,7)azonino(1,2,3-bc)-2-pyridinium-10-yl]vindoline 4-methylbenzenesulfonate.

31. The compound of claim 29 wherein said compound is (4aS,7aR,8S,10R)-15-[3-benzyl-2,4,4a,5,6,7,7a,8,9,10,11,16-dodecahydro-10-(methoxycarbonyl)-1H-indolo(2',3':6,7)azonino(1,2,3-bc)-2-pyridinium-10-yl]vindoline 4-methylbenzenesulfonate.

* * * * *

UNITED STATES PATENT AND TRADEMARK OFFICE
CERTIFICATE OF CORRECTION

PATENT NO. : 4,935,509

DATED : Jun. 19, 1990

INVENTOR(S) : KUEHNE

It is certified that error appears in the above-identified patent and that said Letters Patent is hereby corrected as shown below:

In claim 1 Column 36 line 4, "$-NR_3R_3R_3$, or"

should be $-N\ R_3\ R_3'$ or

Signed and Sealed this

Eighteenth Day of February, 1992

Attest:

HARRY F. MANBECK, JR.

Attesting Officer      Commissioner of Patents and Trademarks